United States Patent [19]
Ruf et al.

[11] Patent Number: 5,994,296
[45] Date of Patent: Nov. 30, 1999

[54] HUMAN MUTANT TISSUE FACTOR COMPOSITIONS USEFUL AS TISSUE FACTOR ANTAGONISTS

[75] Inventors: Wolfram Ruf, San Diego; Thomas S. Edgington, La Jolla, both of Calif.

[73] Assignee: The Scripps Research Institute, La Jolla, Calif.

[21] Appl. No.: 09/035,241

[22] Filed: Mar. 5, 1998

Related U.S. Application Data

[63] Continuation of application No. 08/416,872, filed as application No. PCT/US94/06197, Jun. 1, 1994, Pat. No. 5,726,147, which is a continuation-in-part of application No. 08/070,154, Jun. 1, 1993, abandoned.

[51] Int. Cl.[6] ........................ A61K 38/16; C07K 14/745; G01N 33/53
[52] U.S. Cl. ................................ 514/2; 514/12; 530/350; 530/381; 435/7.1
[58] Field of Search .......................... 514/2, 12; 530/350, 530/381; 435/7.1

[56] References Cited

PUBLICATIONS

Roy, S, Hass, PE, Bourell, JH, Henzel, WJ, Vehar, GA, "Lysine Residues 165 and 166 are Essential for the Cofactor Function of Tissue Factor", J. Biol. Chem. 266(32): 22063–22066, Nov. 15, 1991.

*Primary Examiner*—Karen Cochrane Carlson
*Assistant Examiner*—Holly Schnizer
*Attorney, Agent, or Firm*—Thomas Fitting; Emily Homes

[57] ABSTRACT

The present invention describes a mutant human tissue factor protein which binds functional Factor VII/VIIa but is substantially free of functional procoagulant cofactor activity, and compositions containing the mutant protein. Also disclosed are methods for using the mutant human tissue factor proteins, and recombinant DNA vectors for expressing the protein.

15 Claims, 5 Drawing Sheets

HUMAN MUTANT TISSUE FACTOR COMPOSITIONS USEFUL AS TISSUE FACTOR ANTAGONISTS

This Application is a continuation of application Ser. No. 08/416,872, now U.S. Pat. No. 5,276,147, which was filed as International Application No. PCT/US94/06197, filed Jun. 1, 1994 which is a continuation-in-part Application of application Ser. No. 08/070,154, filed Jun. 1, 1993, now abandoned.

This invention was made with government support under Contract No. HL16411 by the National Institutes of Health. The government has certain rights in the invention.

TECHNICAL FIELD

The present invention relates to a functional mutant of human tissue factor (mhuTF) that binds Factor VII or activated Factor VII (VIIa) but is substantially free of procoagulant cofactor activity. The mutant human tissue factor is useful as a diagnostic and therapeutic reagent.

BACKGROUND

Based on a common folding pattern, proteins may be assigned to fewer than 1000 protein families (Chothia, Nature, 357:543–544 (1992) and Gonnet et al., Science, 256:1443–1445 (1992). Despite the conservation of overall structure, these families of proteins are often characterized by a large repertoire of specificities, as demonstrated, for example, by the immunoglobulin superfamily. Proteinmodules are the building blocks which are conserved within a protein family. Among the receptors for various growth and differentiation regulating hormones, structural predictive algorithms identified a common protein motif, now referred to as the cytokine receptor homology domain as described by Bazan, Proc. Natl. Acad. Sci. USA, 87:6934–6938 (1990) and Thoreau et al., FEBS Lett., 282:26–31 (1991). This domain consists of a pair of structurally similar modules which were proposed to adopt a seven β-strand fold with similarity (Bazan, supra and Patthy, Cell, 61:13–14 (1990) to the domain 2 of CD4 [Wang et al., Nature, 348:411–418 (1990) and Ryu et al., Nature, 348:419–426 (1990)] and to the fibronectin type III repeats [Main et al., Cell, 71:671–678 (1992)]. Experimental support for the proposed structure of the cytokine receptor homology domain was provided by the crystallographic solution of the three dimensional structure of the growth hormone receptor (GHR), a member of this receptor family as described by De Vos et al., Science, 255:306–312 (1992).

Tissue factor (TF) has been predicted to be a distant member of the cytokine receptor family, with structural similarity closer to the interferon receptors [Bazan, supra, and Edgington et al., Thrombosis and Haemostasis, 66:67–79 (1991)] than to the receptors for growth hormone, erythropoietin, colony stimulating factors or several of the interleukins. TF initiates the blood coagulation cascades [Davie et al., Biochem., 30:10363–10370 (1991)] by binding of its ligand, the serine protease Factor VIIa (VIIa) resulting in the formation of a catalytically active enzyme-cofactor complex as described by Edgington et al., supra. In addition, TF serves as a mediator for the auto-activation of VII to VIIa as described by Nakagaki et al., Biochem., 30:10819–10824 (1991).

Upon assembly with TF, VIIa exhibits enhanced catalytic activity evidenced by hydrolysis of small peptidyl [Ruf et al., J. Biol. Chem., 266: 2158–2166, (1991); and Lawson et al., J. Biol. Chem., 267: 4834–4843, (1992)] as well as protein substrates [Ruf et al., J. Biol. Chem., 266: 2158–2166, (1991); and Silverberg et al., J. Biol. Chem., 252: 8481–8488, (1977); Osterud et al., Proc. Natl. Acad. Sci., USA, 74: 5260–5264, (1977); Bom et al., Biochem J., 265: 327–336, (1990); and Lawson et al., J. Biol. Chem., 266: 11317–11327, (1991)]. Cleavage of small peptidyl substrates is efficient with micromolar concentrations of the divalent cation, calcium, $Ca^{2+}$, whereas, the activation of macromolecular substrates such as the zymogen Factor X (X) require the presence of $Ca^{2+}$ at concentrations consistent with saturation of the gamma-carboxylated amino-terminal domain of VIIa [Ruf et al., J. Biol. Chem., 266: 15719–15725, (1991)].

By serving as a cell surface receptor for a protease, TF does not follow the functional paradigm of this receptor family which is characterized by binding of growth and differentiation regulating hormones. Nevertheless, ligand binding by TF is mediated entirely by the structurally conserved extracellular domain [Ruf et al., J. Biol. Chem., 266:2158–2166 (1991) and Ruf et al., J. Biol. Chem., 266:15719–15725 (1991)], as observed for other cytokine receptors as described by De Vos, supra, and Fukunaga et al., EMBO J., 10:2855–2865 (1991).

The assembly of VIIa with its receptor TF results in the formation of a proteolytically competent enzyme-cofactor complex. In order to define the structure which mediates TF function, a combination of antibody, chemical cross-linking and mutational analysis has been applied. See, Ruf et al., Biochem. J., 278:729–733 (1991); Rehemtulla et al., J. Biol. Chem., 266:10294–10299 (1991); Rehemtulla et al., Biochem. J., 282:737–740 (1992); Ruf et al., Proc. Natl. Acad. Sci. USA, 88:8430–8434 (1991); Ruf et al., J. Biol. Chem., 267:6375–6381 (1992); and Ruf et al., J. Biol. Chem., 267:22206–22210 (1992).

As described in the latter reference, a discrete functional region in the carboxyl (C) module of the TF extracellular domain has been extensively characterized by scanning alanine mutagenesis. The detailed analysis of these mutants in the amino acid residue sequence from positions 157–168 demonstrated that residues contributing to function were neither required for high affinity binding of VIIa nor for the enhanced catalytic efficiency of the bound VIIa to hydrolyze small peptidyl substrates. Rather, residues in this particular region specifically contributed to efficient cleavage of the macromolecular substrate Factor X, indicating the existence of functionally important substrate-cofactor interactions.

Based on comparison with GHR and cytokine homology domain, previous studies have implicated the structural modules of TF as the region required for VIIa ligand binding. Sequence-specific antibodies raised against peptides corresponding to residues 40–71 of TF ($C_N$-$C'_N$- and $E_N$-$F_N$-loops) inhibited binding of VIIa to TF as described by Ruf et al., Biochem. J., 278:729–733 (1991). Monoclonal antibodies that completely blocked binding of VIIa have further been assigned to an epitope in the carboxyl aspect of the residue 1–83 sequence. Spatial proximity of residues 44–84 to ligand was further demonstrated by chemical cross-linking to VIIa after complex formation as described by Ruf et al., Proc. Natl. Acad. Sci., USA, 88:8430–8434 (1991). Antibodies to the amino acid residues at positions 94–121 of TF that encompass the inter-module junction have been shown to inhibit the binding of ligand [Ruf et al., Biochem. J., 278:729–733 (1991)], and the $B_C$-$C_C$-loop has been identified as a major cross-linking site in the carboxyl module of TF [Ruf et al., Proc. Natl. Acad. Sci., USA, 88:8430–8434 (1991)]. The $F_C$-$G_C$-loop connects two β-strands that connected by disulfide bonds of two cysteine (Cys) residues in the C-module of TF. Mutational exchange of these Cys residues by Ser results in a mutant protein with diminished affinity for VIIa, consistent with a contribution of the $F_C$-$G_C$-loop to binding of ligand as described by Rehemtulla et al., *J. Biol. Chem.*, 266:10294–10299 (1991).

Roy et al., *J. Biol. Chem.*, 266:22063–22066 (1991), and Ruf et al., *J. Biol. Chem.*, 267:6375–6382 (1991), each described TF mutants having alanine residues substituted into residue positions 165 and 166 in place of the normal human TF amino acid residues at these two positions. In these two mutants, the TF was observed to bind Factor VIIa but exhibit reduced Factor X activation, indicating that positions 165 and 166 are important for Factor X activation activity but not for ligand binding in recombinant TF proteins.

While these antibody, cross-linking and disruptive mutational analyses concordantly implicate both of the structural modules of TF in the high affinity binding of the ligand VIIa, very limited information regarding the requirements for Factor X cleavage activity is available and further the specific TF amino acid residues required for the binding of ligand have yet to be identified. The overall topographical assignment of functional and non-functional regions of TF had not been determined prior to this invention.

BRIEF DESCRIPTION OF THE INVENTION

It has now been discovered that human tissue factor (huTF) contains sites defined by amino acid residues which, when modified, can alter the function of huTF to selectively inactivate the procoagulant cofactor activity of huTF in the huTF:VIIa complex without significantly affecting the ability of the modified huTF to bind Factor VII or VIIa. The modified (mutant) human tissue factor is referred to as mhuTF.

Various amino acid residues in huTF are shown herein to not be essential for high affinity binding to Factor VII or VIIa, whereas those same amino acid residues are important for huTF procoagulant activity.

The selective elimination of the procoagulant activity of mhuTF is advantageous for use as a huTF antagonist because mhuTF described binds available VII or VIIa and forms inactive TF:VIIa complex, thereby blocking VIIa available to form active complex with wild-type huTF. huTF antagonists can be used in vitro or in vivo to inhibit huTF function.

Additionally, mhuTF can be used in a variety of diagnostic settings, such as where inhibition of native huTF is desirable to prevent initiation of the coagulation cascade by the tissue factor pathway. For example, in assays for determining the activation of the coagulation cascade by factors other than tissue factor, it is desirable to assure the inhibition of tissue factor. Assays in which inhibition of tissue factor is preferred are assays for activation of factor IX, assays for Mac-1 receptor-mediated initiation of coagulation, assays for initiation of the contact pathway, and the like.

Thus, in one embodiment, the invention describes a mutant human tissue factor protein (mhuTF) having the capacity to bind Factor VII/VIIa and having at least a 40 percent reduced tissue factor procoagulant cofactor activity. In one embodiment the mhuTf protein is a soluble protein which lacks a membrane anchor. In another embodiment, the mhuTf protein is a membrane-associated protein having a tissue factor membrane anchor.

In a related embodiment, the invention contemplates a therapeutic composition for inhibiting human tissue factor (huTF) comprising a pharmaceutically acceptable carrier and a therapeutic amount of a mutant human tissue factor protein of this invention. Preferred compositions further contain liposomes, cryopreservatives, and/or detergents.

Also contemplated is a method for inhibiting human tissue factor procoagulant activity associated with Factor VII/VIIa comprising contacting Factor VI/VIIa with a mhuTF of this invention in an amount sufficient to inhibit the procoagulant activity of Factor VII/VIIa.

Other related embodiments will be apparent based on the disclosures contained herein.

BRIEF DESCRIPTION OF THE DRAWINGS

In the drawings forming a portion of this disclosure.

DETAILED DESCRIPTION OF THE INVENTION

A. Definitions

Figure 1A:
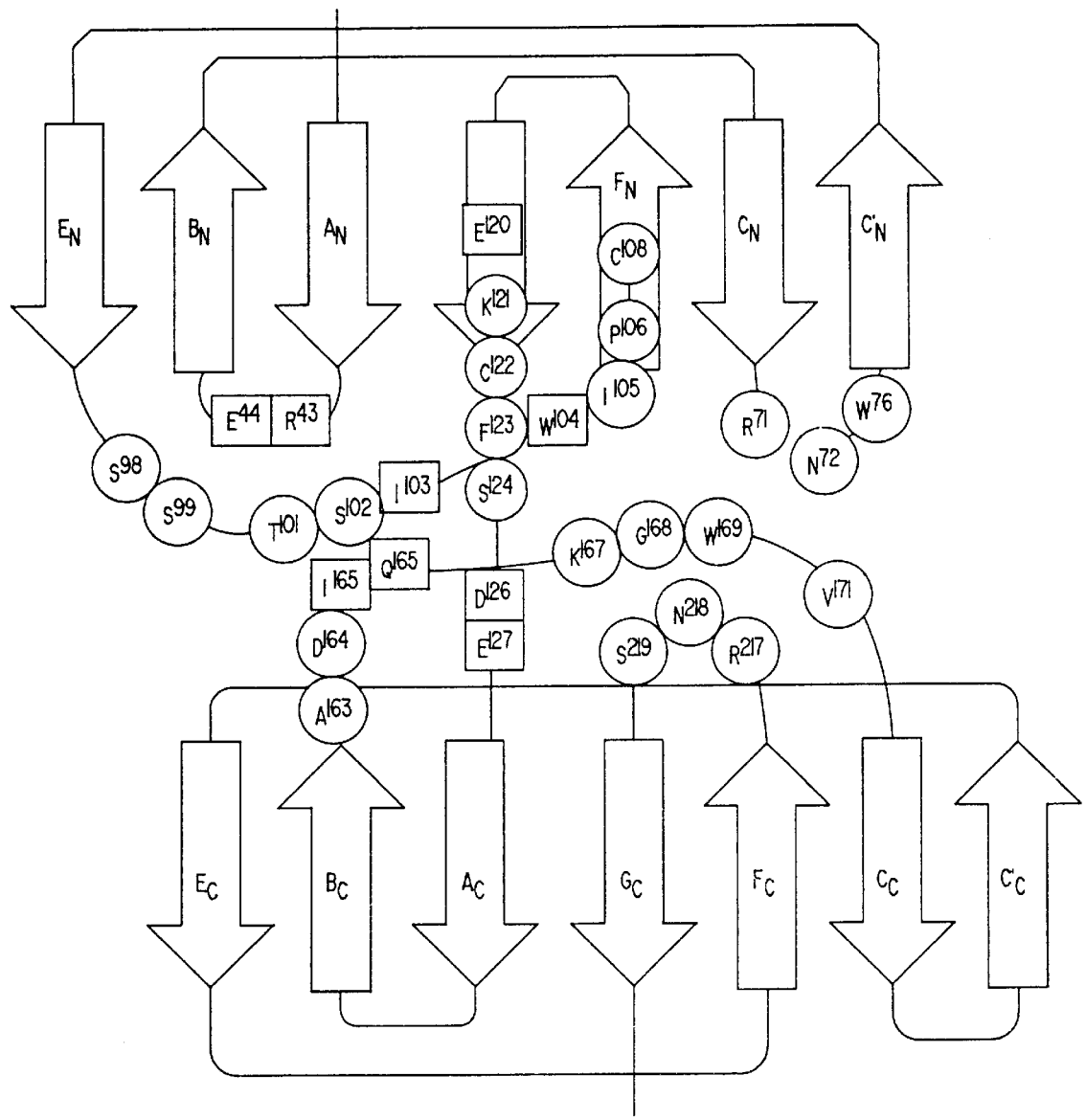
FIGS. 1A and 1B illustrate the comparison of the ligand interfaces in tissue factor (TF) (FIG. 1B) and growth hormone receptor (GHR) (FIG. 1A). A topology diagram is used to show schematically the positions of functionally important residues (circled) in TF, based on alignment of TF with GHR. Residues in GHR which form hydrogen bonds or salt bridges with the hormone (boxed) or which have decreased solvent accessibility (circled) in either of the hormone interfaces are displayed in a similar diagram with data taken from the crystallographic solution of the GHR-growth hormone complex structure.

"Amino acid residue" refers to an amino acid formed upon chemical digestion (hydrolysis) of a polypeptide at its peptide linkages. The amino acid residues described herein are preferably in the "L" isomeric form. However, residues in the "D" isomeric form can be substituted for any L-amino acid residue, as long as the desired functional property is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature (described in *J. Biol. Chem.*, 243:3552–59 (1969) and adopted at 37 C.F.R. 1.822(b)(2)), abbreviations for amino acid residues are shown in the following Table of Correspondence:

TABLE OF CORRESPONDENCE

| SYMBOL | | |
|---|---|---|
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| Z | Glx | Glu and/or Gln |
| W | Trp | tryptophan |
| R | Arg | arginine |
| D | Asp | aspartic acid |
| N | Asn | asparagine |
| B | Asx | Asn and/or Asp |
| C | Cys | cysteine |
| X | Xaa | Unknown or other |

It should be noted that all amino acid residue sequences represented herein by formulae have a left-to-right orientation in the conventional direction of amino terminus to carboxy terminus. In addition, the phrase "amino acid residue" is broadly defined to include the amino acids listed in the Table of Correspondence and modified and unusual amino acids such as those listed in 37 CFR 1.822(b)(4), and incorporated herein by reference. Furthermore, it should be noted that a dash at the beginning or end of an amino acid residue sequence indicates a peptide bond to a further sequence of one or more amino acid residues or a covalent bond to an amino-terminal group such as $NH_2$ or acetyl or to a carboxy-terminal group such as COOH.

"Recombinant DNA (rDNA) molecule" refers to a DNA molecule produced by operatively linking two DNA segments. Thus, a recombinant DNA molecule is a hybrid DNA molecule comprising at least two nucleotide sequences not normally found together in nature. rDNA's not having a common biological origin, i.e., evolutionarily different, are said to be "heterologous".

"Vector" refers to a rDNA molecule capable of autonomous replication in a cell and to which a DNA segment, e.g., gene or polynucleotide, can be operatively linked so as to bring about replication of the attached segment. Vectors capable of directing the expression of genes encoding for one or more polypeptides are referred to herein as "expression vectors". Particularly important vectors allow convenient expression of a mhuTF protein of this invention.

"BHT" refers to butyrated hydroxytoluene.

"CHAPS" refers to 3-[(3-cholamidopropyl)-dimethylammonio]-1-propanesulfonate.

"MOPS" refers to 3-(N-morpholino)-propanesulfonic acid.

"OTG" refers to octyl beta-D-thioglucopyranosides.

"Phospholipid" refers to an organic molecule derived from either glycerol (most commonly) or sphingosine. Phospholipids derived from glycerol (or phosphoglycerides) comprise a glycerol backbone, two fatty acid chains esterified to the first and second carbons of the glycerol and phosphoric acid esterified to the third carbon. Optionally, an alcohol moiety is esterified to the phosphoric acid.

"PC" refers to phosphatidyl choline, an uncharged phosphoglyceride having an alcohol moiety derived from choline is esterified to the phosphoric acid.

"PE" refers to phosphatidyl ethanolamine, a positively charged phosphoglyceride, having an alcohol moiety derived from ethanolamine is esterified to the phosphoric acid.

"PG" refers to phosphatidyl glycerol, a negatively charged phosphoglyceride, having an alcohol moiety derived from glycerol is esterified to the phosphoric acid.

"PS" refers to phosphatidyl serine, a negatively charged phosphoglyceride, having an alcohol moiety derived from serine is esterified to the phosphoric acid.

"rTF" refers to recombinant tissue factor.

"TBS" refers to 20 mM Tris (pH 7.5) containing 150 mM sodium chloride.

B. Mutant Human Tissue Factor

The invention describes a modified (mutant) human tissue factor protein, designated mhuTF, which has the desirable properties of:

(1) high affinity binding to Factor VII or to Factor VIIa; and (2) substantially reduced procoagulant cofactor activity.

By high affinity binding to Factor VII or Factor VIIa is meant that the mhuTF protein has the ability to bind Factor VII or Factor VIIa to a degree that the mhuTF can effectively compete with wild-type (wt) TF when wt-TF is present at physiological concentrations. For a preferred high affinity binding ability, a mhuTF of this invention has an apparent dissociation constant ($K_{Dapp}$ or $K_D$) for binding Factor VIIa in a functional coagulation assay, as described in the Examples, of about 0.1 picomolar (pM) to about 100 nanomolar (nM), preferably about 1 pM to 10 nM, and more preferably about 1–10 pM. When referring to both the active Factor VIIa or inactive Factor VII, the terminology VII/VIIa is used. Representative dissociation constant binding assays for detecting the ability of mhuTF to bind to VII/VIIa are well known and include a typical Scatchard plot analysis, or can be conducted in the form of coagulation assays or chromogenic substrate conversion assays as are described in the Examples. Factor VII or recombinant VIIa for use in a binding assay are commercially available, at least from Novo Nordisk, Inc., (Gentofte, Denmark).

Particularly preferred mhuTF proteins are described herein having a $K_{Dapp}$ in the range of about 1–10 pM, which is about 0.2 to 2 times binding affinity for Factor VII than the affinity of wt-TF for Factor VII. The increased binding constants of mhuTF are particularly preferred at least because they allow the use of smaller amounts of antagonist reagent in methods for inhibiting huTF.

A mhuTF protein of this invention has a substantially reduced procoagulant cofactor activity in order that it perform according to the claimed methods by competing with wt-huTF for binding to Factor VII/VIIa and thereby blocking the ability of wt-TF to bind Factor VII/VIIa and form a catalytically active complex. By substantially reduced procoagulant activity is meant a reduction when compared to wt-TF of activity in any of a variety of coagulation assays such that mhuTF exhibits at least a 40 percent reduction in specific activity (catalytic rate/mass of TF protein). In preferred embodiments, a mhuTF protein exhibits at least a 75% reduction, preferably at least a 90% reduction, and most preferably at least a 99% reduction, in procoagulant cofactor activity as compared to wt-TF when assayed in a conventional coagulation assay. Exemplary assays for measuring the procoagulant cofactor activity of huTF are described in the Examples.

A preferred mhuTF protein comprises a polypeptide that contains the amino acid residue sequence of wt-huTF shown in SEQ ID NO 2 and further contains at least one neutral, non-equivalent or selected semi-conservative amino acid residue substitution, or analog thereof, at an amino acid residue position defined herein to provide the requisite activity. The amino acid residue position(s) at which suitable substitutions may be introduced are readily identifiable by the methods disclosed herein.

A neutral, non-equivalent or selected semi-conservative substitution is a substitution of a native (wild type) amino acid residue for an alternate and chemically dissimilar amino acid residue, thereby altering the primary amino acid residue sequence of wild type huTF. A neutral, non-equivalent or selected semi-conservative residue is an amino acid which substantially changes the chemistry of the side chain of the substituted amino acid residue without disrupting global folding of the protein, local geometry of the peptide backbone, or local packing influences on the interactive structure, but that deletes the extended side-chain atoms necessary for procoagulant cofactor function.

Particularly preferred neutral, non-equivalent or selected semi-conservative substitutions are made in at least one amino acid residue position designated in the wt-huTF at positions selected from the group consisting of S16, T17, S39, T40, S42, D44, V67, L104, E105, T106, R131, R136, D145, V146, F147, V198, N199, R200 and K201. In a particularly preferred mhuTF, the neutral, non-equivalent amino acid residue is an alanine residue substituted in place of the above-identified preferred amino acid residues positions.

Particularly preferred mhuTF proteins of this invention exhibited at least a 75 percent reduction in tissue factor procoagulant cofactor activity when compared to wt-TF, and included an amino acid residue substituted in place of a residue selected from the group consisting of S16, T17, D44, N199, and R200.

In other preferred embodiments, the invention contemplates particular substitutions at residue D44, particularly arginine (R), alanine (A) or glutamic acid (E). Thus, the invention describes mhuTF protein wherein the above substitutions produce a protein having an amino acid residue selected from the group consisting of A44, D44 and R44.

In additional embodiments, selected semi-conservative substitutions are contemplated. In particular, preferred substitution(s) for serine is glycine; for threonine is valine; for lysine is serine, threonine or asparagine; for isoleucine is valine or leucine; for aspartic acid is serine or glycine; for valine is glycine, methionine or leucine; for leucine is serine or isoleucine; for glutamic acid is serine, asparagine or glycine; for arginine is serine or glutamine; for phenylalanine is leucine or isoleucine; and for asparagine is serine, glycine or threonine.

Using conventional terminology, a substitution is indicated by listing the residue to be substituted in single letter code together with the residue position number in the wild type huTF sequence. Thus a mhuTF protein having a substitution of alanine (A) for serine (S) at residue position number 16 is designated as alanine substituted at S16, or A16.

Particularly preferred are the mhuTF proteins described in the Examples, where specific amino acid substitutions were made in the wild type huTF to produce a mutant huTF (mhuTF) having the properties described herein.

For example, the mhuTF proteins having a substitution of arginine (R), alanine (A) or glutamic acid (E) in place of D44, designated as mhuTF R44, mhuTF A44, or mhuTF E44, respectively are particularly preferred.

Additional mhuTF proteins can readily be prepared according to the present methods that contain two or more amino acid residue substitutions as described herein. In particular, it is preferred to combine adjacent or nearby substitutions such as in the preferred construction designated S16-T17-K20 where substitutions of the indicated three amino acid residues are all combined onto a single mhuTF. Other combinations are readily apparent based on the scope of the present disclosure.

Insofar as tissue factor from species other than human are highly related both structurally and in terms of primary sequence, the invention also contemplates mutant tissue factor having the characteristics of mhuTF which are derived from other mammals, including cow, rat, rabbit, mouse, pig, primates, and the like. The primary amino acid residue sequence of non-human tissue factor is known for a variety of the recited mammalian species, including rabbit, mouse and cow. See, for example, Hartzell et al., *Mol. Cell. Biol.*, 9:2567–2573, 1989; Andrews et al., *Gene*, 98:265–269, 1991; and Takayeniki et al., *Biochem. Biophys. Res. Comm.*, 181:1145–1150, 1991.

A mhuTF protein of this invention can be made according to the recombinant DNA methods described herein. The mhuTF protein can be formulated as a soluble protein having the carboxy-terminal membrane anchor portion removed, as described herein. Alternatively, a mhuTF protein can be prepared as an integral membrane protein having a membrane anchor, also as described herein. A mhuTF protein having a complete membrane anchor is typically provided associated with phospholipid compositions, such as in liposome formulations as described further herein.

Thus, in one preferred embodiment, a mhuTF consists essentially of a soluble (truncated) mhuTF protein in which the membrane anchor of wt-TF has been removed, and the above substitution(s) have been introduced. Particularly preferred is a mhuTF in which residues 219–263 have been removed using recombinant DNA methods as described in the Examples.

In another embodiment, a mhuTF consists essentially of a membrane associated (full length) mhuTF protein in which the membrane anchor of wt-TF has present, and the above substitution(s) have been introduced. Particularly preferred is a mhuTF in which residues 1–263 or wt-TF are present, together with the above substitution(s), as described in the Examples.

C. DNA Segments and Vectors

In living organisms, the amino acid residue sequence of a protein or polypeptide is directly related via the genetic code to the deoxyribonucleic acid (DNA) sequence of the structural gene that codes for the protein. Thus, a structural gene or DNA segment can be defined in terms of the amino acid residue sequence, i.e., protein or polypeptide, for which it codes.

An important and well known feature of the genetic code is its redundancy. That is, for most of the amino acids used to make proteins, more than one coding nucleotide triplet (codon) can code for or designate a particular amino acid residue. Therefore, a number of different nucleotide sequences may code for a particular amino acid residue sequence. Such nucleotide sequences are considered functionally equivalent since they can result in the production of the same amino acid residue sequence in all organisms. Occasionally, a methylated variant of a purine or pyrimidine may be incorporated into a given nucleotide sequence. However, such methylations do not affect the coding relationship in any way.

The DNA segments of the present invention are characterized as including a DNA sequence that encodes a mutated human tissue factor protein (mhuTF) according to the present invention. That is, the DNA segments of the present invention are characterized by the presence of a mhuTF structural gene. Preferably the gene is present as an uninterrupted linear series of codons where each codon codes for an amino acid residue found in the mhuTF protein, i.e., a gene free of introns.

One preferred embodiment is a DNA segment that codes an amino acid residue sequence that defines a mhuTF protein corresponding in sequence to a wild type huTF protein except that the amino acid residue sequence has at least one of the substitutions defined herein to provide the requisite activities, and the DNA segment is capable of expressing a mhuTF. A preferred DNA segment codes for an amino acid residue sequence consisting essentially of the sequence shown in SEQ ID NO 2 except that the sequence shown contains nucleotide substitutions necessary to code in the mhuTF for at least one of the substitutions identified herein to produce mhuTF. Representative and preferred DNA segments are described in the Examples.

Homologous DNA and RNA sequences that encode the above mhuTF are also contemplated.

DNA segments (i.e., synthetic oligonucleotides) that encode mhuTF proteins can easily be synthesized by chemical techniques, for example, the phosphotriester method of Matteucci, et al., (*J. Am. Chem. Soc.,* 103:3185–3191, 1981) or using automated synthesis methods. In addition, larger DNA segments can readily be prepared by well known methods, such as synthesis of a group of oligonucleotides that define the DNA segment, followed by hybridization and ligation of oligonucleotides to build the complete segment.

Of course, by chemically synthesizing the coding sequence, any desired modifications can be made simply by substituting the appropriate bases for those encoding the native amino acid residue sequence.

Furthermore, DNA segments consisting essentially of structural genes encoding a mhuTF protein can be obtained from recombinant DNA molecules containing a gene that defines huTF, and can be subsequently modified, as by site directed mutagenesis, to introduce the desired substitutions.

Site-specific primer-directed mutagenesis is now standard in the art, and is conducted using a primer synthetic oligonucleotide complementary to a single-stranded phage DNA to be mutagenized except for limited mismatching, representing the desired mutation. Briefly, the synthetic oligonucleotide is used as a primer to direct synthesis of a strand complementary to the phage, and the resulting double-stranded DNA is transformed into a phage-supporting host bacterium. Cultures of the transformed bacteria are plated in top agar, permitting plaque formation from single cells that harbor the phage.

Thus, by site-directed mutagenesis, one can readily construct any of the described DNA segments that code a mhuTF described herein, by starting, for example, with the expression vector shown in SEQ ID NO 1 that codes and expresses wild type huTF, and mutating selected nucleotides, as described herein, to form one or more of the DNA segments that code a mhuTF of this invention.

In addition, the invention contemplates a recombinant DNA molecule (rDNA) containing a DNA segment of this invention. A rDNA can be produced by operatively linking a vector to a DNA segment of the present invention.

As used herein, the term "vector" refers to a DNA molecule capable of autonomous replication in a cell and to which another DNA segment can be operatively linked so as to bring about replication of the attached segment. A vector capable of directing the expression of a mhuTF gene is referred to herein as an "expression vector". Thus, a recombinant DNA molecule is a hybrid DNA molecule comprising at least two nucleotide sequences not normally found together in nature.

The choice of vector to which a DNA segment of the present invention is operatively linked depends directly, as is well known in the art, on the functional properties desired, e.g., protein expression, and the host cell to be transformed, these being limitations inherent in the art of constructing recombinant DNA molecules. However, a vector contemplated by the present invention is at least capable of directing the replication, and preferably also expression, of the mhuTF structural gene included in DNA segments to which it is operatively linked.

In preferred embodiments, a vector contemplated by the present invention includes a procaryotic replicon, i.e., a DNA sequence having the ability to direct autonomous replication and maintenance of the recombinant DNA molecule extrachromosomally in a procaryotic host cell, such as a bacterial host cell, transformed therewith. Such replicons are well known in the art. In addition, those embodiments that include a procaryotic replicon also include a gene whose expression confers drug resistance to a bacterial host transformed therewith. Typical bacterial drug resistance genes are those that confer resistance to ampicillin or tetracycline.

Those vectors that include a procaryotic replicon can also include a procaryotic promoter capable of directing the expression (transcription and translation) of the mhuTF gene in a bacterial host cell, such as *E. coli,* transformed therewith. A promoter is an expression control element formed by a DNA sequence that permits binding of RNA polymerase and transcription to occur. Promoter sequences compatible with bacterial hosts are typically provided in plasmid vectors containing convenient restriction sites for insertion of a DNA segment of the present invention. Typical of such vector plasmids are pUCS, pUC9, pBR322 and pBR329 available from Biorad Laboratories, (Richmond, Calif.) and pPL and pKK223 available from Pharmacia, Piscataway, N.J.

Expression vectors compatible with eucaryotic cells, preferably those compatible with vertebrate cells, can also be used to form the recombinant DNA molecules of the present invention. Eucaryotic cell expression vectors are well known in the art and are available from several commercial sources. Typically, such vectors are provided containing convenient restriction sites for insertion of the desired DNA segment. Typical of such vectors are pSVL and pKSV-10 (Pharmacia), pBPV-1/pML2d (International Biotechnologies, Inc.), pTDT1 (ATCC, #31255), the vector pCDM8 described herein, and the like eucaryotic expression vectors.

In preferred embodiments, the eucaryotic cell expression vectors used to construct the recombinant DNA molecules of the present invention include a selection marker that is effective in an eucaryotic cell, preferably a drug resistance selection marker. A preferred drug resistance marker is the gene whose expression results in neomycin resistance, i.e., the neomycin phosphotransferase (neo) gene. Southern et al., *J. Mol. Appl. Genet.,* 1:327–341 (1982). Alternatively, the selectable marker can be present on a separate plasmid, and the two vectors are introduced by co-transfection of the host cell, and selected by culturing in the appropriate drug for the selectable marker. Exemplary is the co-transfection described in the Examples.

The invention also contemplates a host cell transformed with a recombinant DNA molecule of the present invention. The host cell can be either procaryotic or eucaryotic, although eucaryotic cells are preferred. Eucaryotic cells useful for expression of a mhuTF protein are not limited, so long as the cell line is compatible with cell culture methods and compatible with the propagation of the expression vector and expression of the mhuTF gene product. Preferred eucaryotic host cells include yeast and mammalian cells, preferably vertebrate cells such as those from a mouse, rat, monkey or human fibroblastic cell line. Preferred eucaryotic host cells include Chinese hamster ovary (CHO) cells available from the ATCC as CCL61, NIH Swiss mouse embryo cells NIH/3T3 available from the ATCC as CRL 1658, baby hamster kidney cells (BHK), and the like eucaryotic tissue culture cell lines. Particularly preferred and exemplary is the CHO-K1 cell line described herein.

Transformation of appropriate cell hosts with a recombinant DNA molecule of the present invention is accomplished by well known methods that typically depend on the type of vector used. With regard to transformation of procaryotic host cells, see, for example, Cohen et al., *Proc. Natl. Acad. Sci. USA,* 69:2110 (1972); and Maniatis et al., *Molecular Cloning, A Laboratory Mammal*, Cold Spring Harbor Laboratory, Cold Spring Harbor, N.Y. (1982).

With regard to transformation of vertebrate cells with vectors containing rDNAs, see, for example, Graham et al., *Virol.,* 52:456 (1973); Wigler et al., *Proc. Natl. Acad. Sci. USA,* 76:1373–76 (1979), and the teachings herein.

Successfully transformed cells, i.e., cells that contain a rDNA molecule of the present invention, can be identified by well known techniques. For example, cells resulting from the introduction of an rDNA of the present invention can be cloned to produce monoclonal colonies. Cells from those colonies can be harvested, lysed and their DNA content examined for the presence of the rDNA using a method such as that described by Southern, *J. Mol. Biol.,* 98:503 (1975) or Berent et al., *Biotech.,* 3:208 (1985).

In addition to directly assaying for the presence of rDNA, successful transformation can be confirmed by well known immunological methods when the rDNA is capable of directing the expression of mhuTF, or by the detection of the biological activity of mhuTF.

For example, cells successfully transformed with an expression vector produce proteins displaying mhuTF antigenicity or biological activity. Samples of cells suspected of being transformed are harvested and assayed for either mhuTF biological activity or antigenicity.

Thus, in addition to the transformed host cells themselves, the present invention also contemplates a culture of those cells, preferably a monoclonal (clonally homogeneous) culture, or a culture derived from a monoclonal culture, in a nutrient medium. Preferably, the culture also contains a protein displaying mhuTF antigenicity or biologically activity.

Nutrient media useful for culturing transformed host cells are well known in the art and can be obtained from several commercial sources. In embodiments wherein the host cell is mammalian, a "serum-free" medium can be used. Preferred is the culturing conditions described herein.

D. Preparation of Mutant huTF

Mutant human tissue factor (mhuTF) of this invention can be produced by a variety of means, and such production means are not to be considered as limiting.

Preparation of a mhuTF typically comprises the steps of: providing a DNA segment that codes a mhuTF protein of this invention; introduction of the provided DNA segment into an expression vector; introduction of the vector into a compatible host cell; culturing the host cell under conditions sufficient for expression of the mhuTF protein; and harvesting the expressed mhuTF protein from the host cell. In preferred embodiments, the harvested mhuTF is reconstituted into phospholipids as described herein to form a composition containing mhuTF. Exemplary procedures for each of the above-enumerated steps are described in the Examples.

Insofar as the expressed protein is highly related to wild type huTF, the purification of mhuTF can be conducted by a variety of art-recognized procedures for preparing purified huTF from cell culture. See, in particular, the purification procedures described herein. In addition, one can use other biochemical fractionation methods to enrich an expressed mhuTF protein and produce purified mhuTF.

Thus, in one embodiment, a mhuTF protein is prepared using a DNA segment as described herein to express mhuTF and subsequently purify the expressed protein. Alternatively, one can use the screening methods described herein to identify additional substitutions of amino acids in the wild type huTF which produce a mhuTF having the disclosed desirable properties. As seen by the numerous mutant constructs described herein, a variety of mhuTF proteins have been designed as produced by the present methods. Additional substitutions (mutations) other than those described specifically herein can be readily designed to form a mhuTF having the disclosed biological activities.

The expressed mhuTF can be formulated into a variety of compositions, both in the form of soluble mhuTF or membrane-associated mhuTF, as described further herein E. Compositions A mutant human tissue factor protein (mhuTF) of the invention is typically provided in one or more of a variety of compositional forms suitable for the contemplated use. In particular, mhuTF can be prepared in the soluble form described herein, with the membrane anchor removed, or can be prepared as a "full-length" membrane-associated form, with the membrane anchor present as described herein.

Although full-length mhuTF retains its biological activity in a variety of buffers and solutions, it is preferred to be formulated in a mild detergent or phospholipid composition. Particularly preferred are phospholipid compositions which afford maximum stability and biological activity of the mhuTF in the composition. Such phospholipid compositions are preferably formulated to form liposome compositions, as are generally well known in the art. Typically, the composition contains an amount of biologically active mhuTF suitable for its contemplated use.

Thus, in one embodiment, the phospholipid composition comprises liposomes having mhuTF associated with the lipid bilayer of the liposomes, such that the mhuTF is inserted through the lipid bilayer.

The lipid bilayer of the liposomes comprises phospholipids, preferably, phosphoglycerides.

Alternatively, according to another aspect of the present invention, mhuTF compositions are provided which comprise phospholipid micelle compositions which have mhuTF associated with phospholipid micelles such that the mhuTF factor is inserted into the micelle.

The mhuTF compositions of the present invention comprise about 0.1 mg to about 3 mg of mhuTF per mg of phospholipid mixture. The ratio of mhuTF to phospholipid mixture may determine the sensitivity of the resulting reagent. Thus, use of a ratio of about 1 to 2 mg mhuTF per mg phospholipid mixture may be suitable for a mhuTF reagent having a International Sensitivity Index ("ISI") of about 1.0. Use of a ratio of about 0.25 to about 0.5 mg mhuTF per mg phospholipid mixture may be suitable to prepare a composition having an ISI of about 1.6 to about 2.0.

Preferred are compositions that additionally comprise from about 0.5 to about 1.5% (w/v) glycine. Where it is desired to be able to lyophilize the mhuTF composition to allow storage and later reconstitution, the reagent preferably includes a cryopreservative, preferably a carbohydrate preservative, most preferably trehalose.

Suitable phospholipids for use in the liposome compositions of the present invention include those which contain fatty acids having twelve to twenty carbon atoms; said fatty acids may be either saturated or unsaturated. Preferred phospholipids for use according to the present invention include phosphatidylcholine (PC), phosphatidylethanolamine (PE), phosphatidylglycerol (PG) and phosphatidylserine (PS). These phospholipids may come from any natural source and the phospholipids, as such, may be comprised of molecules with differing fatty acids. Phospholipid mixtures comprising phospholipids from different sources may be used. For example, PC, PG and PE may be obtained from egg yolk; PS may be obtained from animal brain or spinal chord. These phospholipids may come from synthetic sources as well.

Phospholipid (PL) mixtures having a varied ratio of individual PLs may be used. Suitable PL mixtures comprise (a) from about 20 to about 95 mole percent PC; (b) from about 2.5 to about 50 mole percent PE; (c) from about 2.5 to about 50 mole percent PS; and (d) from about 0 to about 40 mole percent PG. Preferred are PL mixtures comprising from about 5 to 15 mole percent PE, from about 3 to about 20 mole percent PS, from about 10 to about 25 mole percent PG; and the remainder PC, preferably from about 50 to about 90 mole percent PC. Especially preferred are PL mixtures comprising from about 8 to about 12 mole percent PE, from about 3 to about 10 mole percent PS, from about 14 to about 20 mole percent PG and from about 58 to about 75 mole percent PC.

Although the phospholipids may be used in varied ratios, mixtures of phospholipids having preselected amounts of individual phospholipids result in mhuTF compositions having advantageous activity and stability of activity. Although a wide range of ratios of individual phospholipids may be used, for advantageous activity and stability of the resulting mhuTF composition, a certain level of PS in the total phospholipid composition is preferred. The amount of PS that is preferably present to some extent is determined by the remaining components of the PL mixture and their relative amounts as part of the total PL mixture. For example, use of high amounts of PG, another negatively charged phospholipid, (on the order of about 10% or more) allow use of lower levels of PS, on the order of about 3%. However, if a PL mixture low in PS is used, it is advantageous to include at least about 5% PE preferably at least about 10%.

The phospholipids are conveniently combined in the appropriate ratios to provide the PL mixture for use in preparing the mhuTF composition of the present invention. In one preferred embodiment, the PL mixture may comprise PC, PG, PE and PS in the mole ratio of 67: 16: 10: 7, respectively. In another preferred embodiment, the PL mixture may comprise PC, PG, PE and PS in the mole ratio of 7.5: 0: 1: 1, respectively.

The preparation of liposomes is generally well known and has been previously described. Exemplary methods for preparation of mhuTF-containing liposome, includes reverse loading of liposomes (see U.S. Pat. No. 5,104,661), or in the manner described for the incorporation of amphotericin B into lipid vesicles. [See, e.g., Lopez-Berenstein et al., *J. Infect. Dis.*, 151:704–710 (1985); Lopez-Berenstein, *Antimicrob. Agents Chemother.*, 31:675–678 (1987); Lopez-Berenstein et al., *J. Infect. Dis.*, 150:278–283 (1984); and Mehta et al., *Biochem. Biophys. Acta,* 770:230–234 (1984)]. Liposomes with enhanced circulation time may also be prepared as described in U.S. Pat. No. 5,013,556. The disclosures cited herein are hereby incorporated by reference.

Where the mhuTF/liposome composition will be lyophilized prior to storage for later use, it is preferred to include a cryopreservative(s) to protect the integrity of liposomes in the resulting liposome composition during lyophilization and subsequent rehydration. Typical cryopreservatives include a carbohydrate.

Cryopreservation relates to preserving the integrity of delicate substances when liquids containing them are frozen and dehydrated. The use of a carbohydrate as a cryopreservative of liposome integrity upon freezing and subsequent lyophilization has been reported. See, Racker, *Membrane Biol.*, 10:221–235 (1972); Sreter et al., *Biochim. Biophys. Acta.*, 203:254–257 (1970); Crowe et al., *Biochem. J.*, 242:1–10 (1987); Crowe et al., *Biochim. Biophys. Acta.*, 987:367–384 (1988).

Suitable carbohydrate cryopreservatives include trehalose, maltose, lactose, glucose and mannitol. According to a preferred aspect of the present invention, trehalose is included in aqueous buffer solution used in the preparation of the mhuTF composition of the present invention (prior to lyophilization), preferably at a concentration in the range of about 50 mM to about 250 mM.

According to a particularly preferred aspect of the present invention, glycine is included as an additional component of a mhuTF composition. Inclusion of glycine in a mhuTF composition results in reagents which exhibit substantially improved performance in PT assays and other assays such as are described herein, giving reproducible biological activity and increased stability. Thus, a preferred mhuTF composition further comprises from about 0.5 percent to about 1.5 percent (w:v) glycine, and more preferably comprises from about 0.6 to about 1.2 percent glycine.

The phospholipids, which may be obtained from the manufacturer in an organic solvent, are mixed together in the appropriate ratios to yield the specified composition. An antioxidant can also be added to reduce alkyl chain peroxidation of the fatty acid portions of the phospholipids, and the organic solvent, if present, is removed by evaporation. One suitable antioxidant is butyrated hydroxy toluene. Preferably about 0.1% (by weight) of antioxidant is used.

The dried (evaporated) phospholipid mixture is then redissolved with an aqueous detergent solution. Suitable detergents include those which have a relatively high critical micelle concentration (CMC). Womack et al., *Biochim. Biophys. Acta,* 733:210 (1983). Such detergents include detergents having a CMC of greater than approximately 2 mM. Preferred are those detergents having a CMC of between approximately 2 to 25 mM. Such preferred detergents include 3-[(3-cholamidopropyl)-dimethylammonio]-1-propanesulfonate (CHAPS) and alkylglucopyranosides such as octyl beta-D-glucopyranoside, octyl beta-D-thioglucopyranoside and the like. Optionally, the detergent solution may include other components. These components may include buffer salts such as HEPES, Tris, phosphate, and the like; various other salts such as NaCl, KCl, and the like; a carbohydrate cryopreservative such as trehalose, maltose, glucose, and the like; and glycine.

According to a preferred embodiment of the present invention, the detergent solution comprises 20 mM Tris, pH 7.5, 150 mM NaCl, (TBS) containing 100 mM CHAPS, 150 mM trehalose and 0.8% glycine. According to this preferred embodiment, the phospholipids are redissolved in this solution to give a final concentration of about 20 mg/ml.

Expressed and purified mhuTF, together with carrier protein, are combined with the redissolved phospholipids and the volume of the resulting mixture is adjusted with a buffer as described above, preferably containing cryopreservative (most preferably trehalose) and glycine but no detergent. mhuTF is admixed with carrier protein, such as bovine gamma globulin, and sufficient buffer is added to adjust the final concentrations of tissue factor to 10 µg/ml, bovine gamma globulin to 1 mg/ml, phospholipid to 4 mg/ml and detergent to 20 mM. Suitable buffers include TBS containing 150 mM trehalose and 0.8% glycine.

The resulting clear, colorless solution requires no vortexing or sonicating to ensure co-solubilization.

The detergent in the phospholipid-mhuTF admixture can be removed by a number of methods resulting in a stable liposome composition having mhuTF associated with and inserted through the lipid bilayer. Suitable methods of removal of detergent include dialysis, tangential flow diafiltration, cross flow hollow fiber filtration, treatment with hydrophobic chromatography resin, and simple dilution.

One preferred method of detergent removal from the phospholipid-mhuTF admixture utilizes dialysis for at least 30 hours at room temperature in dialysis membrane tubing against a buffer such as TBS containing 150 mM trehalose, 0.8% glycine and 0.05% $NaN_3$ to remove the detergent. Another preferred method of detergent removal utilizes resin treatment. Suitable resins include hydrophobic chromatographic resins such as Amberlite XAD-2 (Rohm and Haas Co. in Philadelphia, Pa.) or Bio-Beads SM-2 (BioRad in Richmond, Calif.). The resins may be used to remove the detergent, either by direct contact with the phospholipid-mhuTF solution admixture or separated from it by a dialysis membrane. The rate of removal of detergent from the phospholipid-mhuTF admixture is proportional to the weight ratio of the detergent in solution and the chromatographic resin beads.

The liposome solution resulting from the detergent removal step is then made to 5 mM $CdCl_2$. According to one preferred aspect, the liposome composition which contains the fully active mhuTF is diluted to a concentration 50 mM Tris, pH 7.5, 75 mM trehalose, 0.8% glycine and 10 to 15 mM $CaCl_2$ before use. Alternatively, the diluted reagent may be lyophilized for long term preservation of its biological performance characteristics and then later reconstituted by suspension in water before use.

Another preferred method of detergent removal avoids the use of either dialysis or resin treatment and yet provides for preparation of active mhuTF reagent. According to this method, detergent solubilized phospholipid compositions containing mhuTF are diluted into a buffer without detergent to produce mixed micelles containing mhuTF which remain capable of being activated by $CdCl_2$. According to this aspect of the invention, phospholipids are dissolved to 20 mg/ml in a buffer containing detergent, preferably an alkyl glucopyranoside. A suitable buffer-detergent solution comprises 20 mM HEPES (pH 6) containing 50 mM octyl beta-D-thioglucopyranoside (OTG) and 150 mM NaCl. Carrier protein, mhuTF, and $CdCl_2$ are then added and the mixture diluted further with buffer without detergent, such as 20 mM HEPES (pH 6) containing 150 mM NaCl, to yield final concentrations of mhuTF at 10 µg/ml, carrier protein (bovine gamma globulin) at 1 mg/ml, $CdCl_2$ at 5 mM, phospholipids at 4 mg/ml, and OTG at 10 mM. The reagent may be lyophilized for storage as described above, or diluted as described above before use.

According to another aspect of the present invention, this reagent may be prepared by following methods for the preparation of vesicles and detergent-phospholipid mixed micelles from phospholipids by methods based on mechanical means, by removal of organic solvents, by detergent removal, and by size transformation as has been described by Lichtenberg et al, *Methods of Biochemical Analysis*, 33:337–462 (1988), and the disclosures of which are incorporated herein by reference.

1. Therapeutic Compositions

Insofar as the present invention also contemplates therapeutic uses of a mhuTF protein of this invention, therapeutic compositions useful for practicing the therapeutic methods are also contemplated. Therapeutic compositions of the present invention contain a physiologically tolerable carrier together with at least one species of mhuTF as described herein, dissolved or dispersed therein as an active ingredient. In a preferred embodiment, the therapeutic composition is not immunogenic when administered to a human patient for therapeutic purposes.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects such as nausea, dizziness, gastric upset and the like.

The preparation of a pharmacological composition that contains active ingredients dissolved or dispersed therein is well understood in the art. Typically such compositions are prepared as sterile injectables either as liquid solutions or suspensions, aqueous or non-aqueous, however, solid forms suitable for solution, or suspensions, in liquid prior to use can also be prepared. The preparation can also be emulsified. Particularly preferred are phospholipid and liposome compositions as described herein. In addition, a therapeutic amount of mhuTF can be present in a ointment or on a diffusible patch, such as a bandage, as to afford local delivery of the agent.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, or the like and combinations thereof. In addition, if desired, the composition can contain minor amounts of auxiliary substances such as wetting or emulsifying agents, pH buffering agents and the like which enhance the effectiveness of the active ingredient.

The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, propylene glycol, polyethylene glycol and other solutes.

Liquid compositions can also contain liquid phases in addition to and to the exclusion of water, as described herein. Exemplary of such additional liquid phases are glycerin, vegetable oils such as cottonseed oil, organic esters such as ethyl oleate, and water-oil emulsions, particularly the liposome compositions described earlier.

A therapeutic composition contains an effective amount of mhuTF of the present invention, typically an amount of at least 0.1 weight percent of active protein per weight of total therapeutic composition. A weight percent is a ratio by weight of mhuTF protein to total composition. Thus, for example, 0.1 weight percent is 0.1 grams of mhuTF per 100 grams of total composition.

F. Diagnostic Methods

The present invention contemplates various assay methods for analyzing components of the coagulation cascade through the use of a mhuTF composition of this invention. Particularly preferred are assays for analyzing activation of coagulation by means other than with Factor VIIa and huTF. Another preferred embodiment is the use of mhuTF compositions for ELISA or other immunoassays instead of using anti-VII antibodies.

Those skilled in the art will understand that there are numerous well known clinical diagnostic coagulation chemistry procedures in which the described mhuTF composition of this invention can be used. Thus, while exemplary assay methods are described herein, the invention is not so limited.

A preferred assay is the analysis of the activation of coagulation by measuring the kinetics of the activation of factor IX by TF-independent means as described by Gailani et al., *Science,* 253:909–912 (1991). The mhuTF reagents of this invention as used in this assay bind to Factor VII or VIIa preventing wild-type TF from forming an active TF-VII or TF-VIIa complex thereby inhibiting the extrinsic coagulation pathway allowing the determination of the amount of activated factor IX formed.

Another preferred assay in which mhuTF compositions are utilized is in assays for measuring the TF-independent pathway of coagulation mediated by the macrophage cell surface integrin receptor, Mac-1, as described by Altieri et al., *Proc. Natl. Acad. Sci., USA,* 85:7462–7466 (1988) and Altieri et al., *J. Biol. Chem.,* 264:2969–2972 (1989). Mac-1 is a receptor for fibrinogen in a reaction linked to fibrin deposition on the surface of monocytes. As used in this assay, the mhuTF reagents of this invention allow the determination of Mac-1-mediated clotting without the confounding of coagulation mediated by an active TF-VII or TF-VIIa complex.

A further preferred diagnostic assay is the use of mhuTF compositions in assays for measurement of contact or surface activation pathway components in which kallikreins and factor XIIa are involved. With the extrinsic pathway blocked through the use of an inactive mhuTF-VII or mhuTF-VIIa complex, the activation of both factor XII and kallikrein can be determined without interference.

In the contemplated diagnostic assays described above, the components of the assays can vary so long as the addition of a mhuTF reagent results in the binding of Factor VII or Factor VIIa resulting in the formation of an inactive TF-VII or TF-VIIa complex. The formation of an inactive TF-VII or TF-VIIa complex results in the inhibition of procoagulant activity thereby allowing for the determination of activation of coagulation mediated by other coagulation cascade proteins.

An alternative preferred diagnostic assay is an ELISA or other immunoassay format where the mhuTF reagents are used in place of an anti-VII antibody reagent for assaying the amount of Factor VII or VIIa. While an antibody binds to particular antigen based on a structural reaction between an antibody combining site and an antigen, a mhuTF protein binds to Factor VII or VIIa in a functional manner requiring the presence of calcium. Thus, the diagnostic method described herein comprises the capture of VII or VIIa without clotting plasma in a functional manner rather than structural that requires native binding interactions. In one embodiment, the mhuTF, provided in the solid phase, captures VII or VIIa in the presence of calcium. The amount of captured VII or VIIa is then determined by a second reaction with a detecting polyclonal anti-VII antibody reagent.

G. Diagnostic Kits

The present invention also describes a diagnostic system, preferably in kit form, for assaying for the presence and/or amount of one or more of the members of a coagulation cascade in a sample according to the diagnostic methods described herein. A diagnostic system includes, in an amount sufficient to perform at least one assay, a subject mhuTF composition, as a separately packaged reagent.

Instructions for use of the packaged reagent are also typically included.

"Instructions for use" typically include a tangible expression describing the reagent concentration or at least one assay method parameter such as the relative amounts of reagent and sample to be admixed, maintenance time periods for reagent/sample admixtures, temperature, buffer conditions and the like.

A diagnostic system of the present invention can also include a one or more of the other reagents used in the preparation of a clotting time assay as described herein, in an amount sufficient for at least one assay.

The reagent species of any diagnostic system described herein can be provided in solution, as a liquid dispersion or as a substantially dry power, e.g., in lyophilized form. A solid support such as the before-described microtiter plate and one or more buffers can also be included as separately packaged elements in this diagnostic assay system.

The packaging materials discussed herein in relation to diagnostic systems are those customarily utilized in diagnostic systems, and can be formulated for single assay use, multiple assay use, manual or automated assay protocols, and the like.

The term "package" refers to a solid matrix or material such as glass, plastic (e.g., polyethylene, polypropylene and polycarbonate), paper, foil and the like capable of holding within fixed limits a diagnostic reagent such as a mhuTF composition of the present invention. Thus, for example, a package can be a bottle, vial, plastic and plastic-foil laminated envelope or the like container used to contain a contemplated diagnostic reagent.

The materials for use in the assay of the invention are ideally suited for the preparation of a kit. Such a kit may comprise a carrier means being compartmentalized to receive in close confinement one or more container means such as vials, tubes, and the like, each of the container means comprising one of the separate elements to be used in the method. For example, one of the container means may comprise a mhuTF composition of the invention. The kit may also have containers containing any of the other above-recited immunochemical reagents used to practice the diagnostic methods.

H. Therapeutic Methods

In view of the ability of mhuTF to bind Factors VII or VIIa and inhibit wild-type (wt) huTF as demonstrated herein, mhuTF of this invention can be used therapeutically as a huTF antagonist to prevent wt-TF from forming a biologically active procoagulation complex with Factor VII/VIIa. Inhibition of wt-TF is desirable where the reduction of Factor VIIa-dependent coagulation is indicated.

The method comprises contacting, in vivo or in vitro, a sample believed to contain one or more precursors to a procoagulation complex (e.g., wt-TF or Factor VII/VIIa) with a therapeutic composition of this invention containing an amount of mhuTF sufficient to inhibit the procoagulant cofactor activity of huTF. In one embodiment, the contacting in vivo is accomplished by administering a therapeutically effective amount of a physiologically tolerable composition containing mhuTF of this invention to a patient, thereby inhibiting wt-huTF present in the patient.

Thus, the present invention describes in one embodiment a method for inhibiting tissue factor-mediated coagulation in a human comprising administering to the human a therapeutically effective amount of the mhuTF of this invention.

A representative patient for practicing the present methods is any human at risk for coagulation.

A therapeutically effective amount of a mhuTF is a predetermined amount calculated to achieve the desired effect, i.e., to bind Factor VII/VIIa present in the patient, and thereby compete with wt-TF for binding and form a procoagulant complex that is enzymatically defective, decreasing the likelihood of coagulation in the patient. In the case of in vivo therapies, an effective amount can be measured by improvements in one or more symptoms associated with huTF-dependent coagulation.

Thus, the dosage ranges for the administration of a mhuTF of the invention are those large enough to produce the desired effect in which the symptoms of coagulated are ameliorated or the likelihood of coagulation are decreased. The dosage should not be so large as to cause adverse side effects, such as hyperviscosity syndromes, pulmonary edema, congestive heart failure, and the like. Generally, the dosage will vary with the age, condition, sex and extent of the disease in the patient and can be determined by one of skill in the art.

The dosage can be adjusted by the individual physician in the event of any complication.

A therapeutically effective amount of an mhuTF of this invention is typically an amount such that when administered in a physiologically tolerable composition is sufficient to achieve a plasma or local concentration of from about 1 picomolar (pM) to 1,000 nanomolar (nM), preferably about 100 pM to about 50 nM, and most preferably about 1 to 30 nM.

The mhuTF of the invention can be administered parenterally by injection or by gradual infusion over time. The mhuTF of the invention can be administered intravenously, intraperitoneally, intramuscularly, subcutaneously, intracavity, transdermally, dermally, and can be delivered by peristalic means.

The therapeutic compositions containing a mhuTF of this invention are conventionally administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgement of the practitioner and are peculiar to each individual. However, suitable dosage ranges for systemic application are disclosed herein and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

EXAMPLES

The following examples relating to this invention are illustrative and should not, of course, be construed as specifically limiting the invention. Moreover, such variations of the invention, now known or later developed, which would be within the purview of one skilled in the art are to be considered to fall within the scope of the present invention hereinafter claimed.

1. Construction of a Tissue Factor Expression Vector and Site-Directed Mutagenesis to Produce Human Tissue Factor Mutants (mhuTF)

Tissue factor (TF), the initiating cell surface receptor molecule of the coagulation cascades, has been predicted to be a distant member of the cytokine receptor family which consists of structurally related receptors characterized by a homology unit of a pair of seven β-strand modules in their extracellular domains. Tissue factor binds to and changes the catalytic efficiency of coagulation Factor VIIa. To localize the site for ligand interaction, approximately half of the residues in the two putative extracellular domain modules of tissue factor were replaced by alanine (Ala).

With the exception of Pro, Gly and Cys, Ala has proven to be a structurally conservative replacement for most amino acids because this exchange generally preserves the peptide backbone geometry and global conformation thus allowing the evaluation only of side chain function. See, Bass et al., Proc. Natl. Acad. Sci., USA, 88:4498–4502 (1991), Eriksson et al, Science, 255:178–183 (1992), and Heinz et al., Proc. Natl. Acad. Sci. USA, 89:3751–3755 (1992). Multiple Ala substitutions were used to define the functional residues for TF ligand binding guided by the identification of sequence spans implicated in function by antibody and cross-linking experiments.

A model based on the predicted architectural similarity of TF to the growth hormone receptor (GHR) as described by Bazan, Proc. Natl. Acad. Sci., USA, 87:6934–6938 (1990) was used to primarily focus on predicted loops which connect β-strands. The topology of β-strands is based on the GHR amino- (N) or carboxyl-terminal (C) modules as shown in FIG. 1A; all structural elements of TF referred to hereafter are those predicted from this model. Whereas the initial analysis involved random searching of the predicted loop regions, the subsequent mutations were specifically targeted to single residues in spatial proximity to identified functional regions including residues in predicted β-strands.

To delineate the functional and non-functional regions, the mutational mapping implicitly assumed that the ligand site in TF follows the general rules for protein-protein interactive regions. These are characterized by discontinuous sequence spans which provide multiple contacts between ligand and receptor as described by Janin et al., *J. Biol. Chem.*, 265:16027–16030 (1990). As demonstrated by the mutational analysis of the GHR as described by De Vos et al., *Science*, 255:306–312 (1992) and Bass et al., *Proc. Natl. Acad. Sci., USA,* 88:4498–4502 (1991), Ala replacements of contact or other residues in the ligand interface typically affect the affinity of complex formation less than 100-fold, since the overall affinity results from the additive effects of multiple contacts as shown by Wells, *Biochem.*, 29:8509–8517 (1990). Assignment of a functional site by mutational mapping thus relies on the identification of several functionally important residues which are in sufficient proximity to form a more or less contiguous area on the protein surface. Site-directed mutagenesis as described herein of native human TF, thus, resulted in the production of the mutant human TF (mhuTF) proteins for use in determining the region for ligand interaction in tissue factor.

A. Construction of the pCDM8 Expression Vector Containing the Human TF Coding Sequence To construct an expression vector for subsequent mutagenesis and expression of tissue factor proteins, the cDNA containing the complete TF nucleotide coding sequence was ligated into the expression vector pCDM8 described by Seed, *Nature*, 329:840–842 (1987). The pCDM8 vector contained the following elements: a simian virus 40 (SV40) derived origin of replication; the eucaryotic transcription regulatory elements, splice and poly(A)+; a bacterial episome origin of replication; a procaryotic genetic marker (supF, suppressor tRNA gene); a polyoma origin of replication, bacteriophage M13 origin of replication, and the cytomegalovirus promoter (CMV).

The 775 base pair (bp) EcoR I fragment containing the cDNA (nucleotides 1 to 775) encoding amino acid residues 1–215 of TF was excised from the plasmid CTF545 prepared as described by Morissey et al., *Cell,* 50:129–135 (1987), the disclosure of which is hereby incorporated by reference. This resulting fragment was ligated into the 505 bp EcoR I-Hind III fragment of pCTF439 consisting of nucleotides 776 to 1280 that encoded the amino acid residues of TF from 216–263 and the concatenated DNA was then cloned into pUC19 to yield the construct pCTF153 as described by Rehemtulla et al., *Thrombosis and Haemostasis,* 65:521–527 (1991), the disclosure of which is hereby incorporated by reference. The resulting fragment was then cloned into pUC18 using BamH I linkers to form pCTF1200. The sequence of this construct confirmed the presence of the entire coding region of native human TF in addition to 360 bp of untranslated 3' region and 38 bp of untranslated 5' sequence.

For expression of full-length wild-type and mutant TF proteins in Chinese Hamster Ovary cells (CHO), the BamH I insert from pCTF1200 was excised, blunt-ended using Klenow fragment of DNA polymerase and ligated into the vector pCDM8 prepared as described above that had been digested with Xho I and blunt-ended with Klenow. The resultant construct, designated pETF1773, contained the TF cDNA in an orientation that allowed transcription under the control of the strong CMV promoter of pCDM8. The complete nucleotide sequence of the pCDM8 vector containing the TF cDNA insert is listed in SEQ ID NO 1. The nucleotide sequence encoding the signal peptide of TF begins at nucleotide position 2267 and ends at 2362 followed by the nucleotide sequence encoding TF beginning at 2363 and ending at 3154. The encoded 263 amino acid residue sequence of the nonmutagenized native human TF is listed in SEQ ID NO 2.

The wild-type and mutant TF proteins were also expressed as soluble truncation mutants having amino acid residues 1–218 as shown in SEQ ID NO 2. The soluble truncation mutants were expressed in the yeast expression system, *Saccharomyces cerevisiae*. The coding sequence for residues 1–218 was obtained by using polymerase chain reaction (PCR) amplification on the pCDM8 mammalian cell expression plasmids into which mutations had been amplified as described below in Example 1B. PCR was performed as described in "Current Protocols In Molecular Biology", Ausebel et al, eds, Unit 15.1.1–15.1.4, Wiley and Sons, New York (1987). The 5' sense and the 3' anti-sense oligonucleotide primers, respectively Y2 and Y6, were synthesized by The Scripps Research Institute Core Facility with the respective nucleotide sequences, 5'-GGGGTATCTTTGGATAAAAGATCAGGCACTACAAATACTGTG- (SEQ ID NO 3) and 5'-GCAGCCAAGCTGGCCTCGAAGTTATCTGAATTCCCCTTTCTC( (SEQ ID NO 4). In addition, each amplification using the 3' primer resulted in changing the triplet, GAA, encoding the glutamic acid amino acid residue at position 219 in SEQ ID NO 2, to a termination codon.

The resultant amplified products for encoding the truncated forms of mutated TF were then separately subcloned into the Stu I site of the *E. coli/S. cerevisiae* shuttle vector, pMFalpha8, as described by Miyajima et al., *Gene*, 37:155–161 (1985), the disclosure of which is hereby incorporated by reference. The pMFalpha8 expression vector contained yeast DNA, including the promoter of the mating pheromone and its downstream leader sequence along with the TRP5 terminator. The subcloning of the TF constructs into pMFalpha8 was accomplished with in vivo recombination performed as described by Jones et al., *BioTechniques*, 10:62–66 (1991) and well known to one of ordinary skill in the art.

B. Mutagenesis of TF

Oligonucleotide directed mutagenesis was performed using the uracil substitution method according to Kunkel, *Proc. Natl. Acad. Sci., USA,* 82:488–492 (1985) and also described in Ausebel et al., *Current Protocols in Molecular Biology*, Unit 8, Wiley and Sons, New York, (1990). The following modifications to the basic site-directed mutagenesis procedure were performed to adapt the procedure for use with the pCDM8 expression vector as described by Rehemtulla et al., *J. Biol. Chem.*, 266:10294–10299 (1991). Phosphorylated mutagenic oligonucleotides (10 nanograms (ng)) were separately annealed to 100 ng of single-stranded pCDM8 template in which entire TF-encoding nucleotide sequence had been cloned. The single-stranded template was isolated from the host cells, *E. coli* strain CJ236/p3 (Invitrogen, San Diego, Calif.). Annealing was performed in 20 millimolar (mM) Tris-HCl at pH 7.4 containing 2 MM $MgCl_2$ and 50 mM NaCl at 70 degrees Celsius (70C.) and thereafter cooled to room temperature. The second strand was synthesized using T4 DNA polymerase and T4 DNA ligase (Boehringer Mannheim, Indianapolis, Ind.) in 10 mm Tris-HCl at pH 7.5 containing 5 mM $MgCl_2$, 2 mM dithiothreitol, 5 mM deoxynucleotide triphosphates and 10 mM ATP in a cycle of 5 minutes at 4C., 5 minutes at room temperature, and 90 minutes at 37C. One-fifth of the reaction was then transformed into MC1061/p3 as described by Seed et al., supra, and transformants were screened for the presence of mutant sequences by restriction enzyme analysis to detect newly introduced restriction sites, if applicable. Sequencing of mutant constructs was accomplished using single-stranded DNA rescued from the strain XS127 and the helper phage R408. The Sequenase system (US Biochemical, Cleveland, Ohio) was used to perform dideoxynucleotide sequencing.

For the PCR site-directed mutagenesis procedure described above, oligonucleotide primers were designed to result in the incorporation of nucleotide sequences that encoded alanine substitutions in the TF gene-encoded protein. Oligonucleotide primers were thus designed to amplify the triplet codon for encoding an alanine amino acid residue into the nucleotide sequence at a preselected triplet encoding a normal TF amino acid residue. For example, the oligonucleotide primer, K20, was designed to substitute the lysine amino acid residue at position 20 with alanine. The designation K20 indicates the single letter amino acid code for the amino acid residue at the indicated position in the TF protein. K20 had the nucleotide sequence 5'-CTAATTTC GCGACAATTT-3' (SEQ ID NO 5). The triplet for introducing the desired amino acid substitution a: position 20 is underlined. The original nucleotide sequence for encoding the lysine residue was AAG as shown in SEQ ID NO 1 at nucleotide positions 2420–2422. The remaining sequence in the K20 primer is identical to that listed in SEQ ID NO 1 for encoding TF beginning at nucleotide position 2412 and ending at position 2429.

For preparing the remaining alanine-containing TF mutated proteins of this invention as indicated in FIG. 2, oligonucleotides were prepared in the same manner as described above for K20, the design of which is easily accomplished to one having ordinary skill in the art. The amino acid residues in TF that were mutagenized to alanine residues are shown in FIG. 2 indicated by the vertical closed bars graphed above the normal TF amino acid residue sequence.

Other oligonucleotide primers for use in this invention were designed to incorporate more than one alanine substitution in a region of TF protein. Three such oligonucleotide primers were prepared. The primer designated S16-T17-K20 had the nucleotide sequence 5'-CTTGGAAA GCAGCTAATTTCGCGACAATTT-3' (SEQ ID NO 6) for incorporating alanine residues at amino acid residue positions 16, 17 and 20 of the normal TF protein as indicated by the underlined triplets. Similarly, the primer designated S39-T40-S42 had the nucleotide sequence 5'-GTTCAAATA GCTGCTAAGGCAGGAGAT-3' (SEQ ID NO 7) that provided for alanine residues at amino acid residue position 39, 40 and 42 of TF. A third triple alanine TF mutant was generated with an oligonucleotide primer designated K65-D66-K68 with the nucleotide sequence 5'-GAGATTGTG GCTGCAGTGGCGCAGACGTAC-3' (SEQ ID NO 8). A TF mutant having any combination and number of alanine substitutions is easily accomplished by one having ordinary skill in the art through the design of oligonucleotide primers as described herein. Each of the PCR amplified mutations was subsequently confirmed by DNA sequencing of CsCl-purified plasmid DNA.

TF mutants that encoded full-length (263 amino acid residues) alanine-substituted TF were obtained by the PCR-mutagenesis procedure. When the cells were induced to express as described below, the expressed full-length TF mutants were not secreted from the cells thereby requiring purification from a cell lysate as described in Example 2A. In order to produce a soluble secreted form of the TF mutants, a truncated form of each mutagenized TF nucleotide sequence was produced by PCR as described in Example 1A and expressed in *S. cerevisiae* yeast shuttle vector, pMFalpha8, as described below.

C. Expression of Mutant TF Constructs

1) Mammalian Expression System

For the production of stable cell lines, Chinese Hamster Ovary cells (CHO-K1) having an ATCC Accession No CCL61 were grown in Dulbecco's modified Eagles medium (DMEM), 10% newborn calf serum (HyClone Laboratories, Logan Utah), 2 mM 1-glutamine, 0.1 mM proline, 100 U/ml penicillin and 100 microgram/milliliter (ug/ml) streptomycin. The prepared cells were transfected using the calcium phosphate precipitation method and stable cell lines were generated by separately cotransfecting, at a 1:20 ratio, 1 ug of a neomycin resistance gene for selection purposes (pMAMneo, Clontech Laboratories, San Francisco, Calif.) with 20 ug of each of the purified mutagenized plasmids prepared in Example 1B encoding the described mutations. The DNA was first diluted in 250 mM $CaCl_2$ then precipitated by drop-wise addition of 2× Hepes buffered saline (0.25 M NaCl, 40 mM Hepes, 0.7 mM $Na_2HPO_4$ at pH 7.05 with 0.5 M NaOH) followed by vigorous vortexing and then incubation at room temperature for 20 minutes. The DNA precipitate was then added to a monolayer to CHO-K1 cells. After maintenance at 37C. for 4 hours, the cells were treated with 2 ml of 10% glycerol in medium for 3 minutes and then washed three times with PBS (10 mM sodium phosphate at pH 7.4 and 0.15 M NaCl). The washed cells were then maintained with fresh medium for 36 hours for preparing transient transfections.

To select for transfectants and maintain stable cell lines, 36 hours after transfection, the cultures were suspended and diluted to a density of $10^4$ cells/100 mm petri dish. The medium was supplemented with 600 ug/ml G418 (Geneticin, Gibco, Gaithersburg, Md.) and the cells were replated in petri dishes. Fresh medium was added to the cells after 7 days and G418 resistant colonies appeared after 10–14 days. Single colonies were picked using cloning cylinders and grown in large cultures for analysis. Tunicamycin (Sigma, St. Louis, Mo.) treatment of the cells was performed at 1 ug/ml for 48 hours.

2) Yeast Expression System

Expression of exogenous proteins from pMFalpha8 described in Example 1A resulted in the secretion into the culture medium of a gene-encoded and processed mature protein product, in this instance, truncated TF wild-type or mutant proteins of this invention.

For expression, yeast strain GRY697 (MATð, trp1-1Δ, ura3-52) was transformed with the PMFalpha8 expression plasmid containing the TF truncation mutant. Transformed cells were selected on tryptophan-deficient culture plates.

2. Expression of Tissue Factor Mutants from the Mutagenized Expression Vectors

A. Mammalian Expression System

The stable cell lines expressing the full-length mutant TF proteins prepared in Example 1C were then grown to allow for purification of the recombinant mutant TF. To accomplish this, the stable cells lines were separately grown in 2 liter spinner flasks in Excell 301 (JR Scientific, Woodland, Calif.), 10% newborn calf serum, 2 mM L-glutamine, 0.1 mM proline, 100 U/ml penicillin and 100 ug/ml streptomycin. Cells were harvested at maximum density and lysed in 200 ml of 1% Triton X-100 in TBS. After complete lysis, insoluble debris was pelleted at 10,000×g at 4C. for 20 minutes. The resultant supernatant was applied to an immuncaffinity column on which the anti-TF monoclonal antibody, TF8-5G9, was coupled to Affigel beads (Bio-Rad, Hercules, Calif.) as described by Morissey et al., *Cell*, 50:129–135

(1987), the disclosure of which is hereby incorporated by reference. The unbound material was washed from the column using TES, 0.1% Triton X-100 and followed by 0.1 M glycine at pH 4.5, containing 0.1% Triton X-100.

The TF mutant proteins were separately eluted with 0.1 M glycine at pH 2.5 containing 0.1% Triton X-100. Fractions containing the eluted mutant TF proteins were immediately neutralized to pH greater than 5.5 and rapidly dialyzed against 0.01% Triton X-100 in TBS for storage at −70C. Concentration of the eluted proteins was determined by immunoassay and by direct protein using the BCA protein assay (Pierce, Rockford, Ill.). All assays were standardized with purified natural human TF quantitated by amino acid composition based on a protein mass of 29,593 as described by Morissey et al., supra.

Wild-type TF was also purified as described above. Expression of mutant TF ranged from 0 to 970 ng per $10^6$ cells equivalent to that seen with normal TF as described by Rehemtulla et al., *Thrombosis and Haemostasis*, 65:521–527 (1991).

B. Yeast Expression System

The yeast-expressed truncated forms of mutant TF proteins were purified from the yeast culture broth by immunoaffinity chromatography on the TF8-5G9 monoclonal antibody column as described above with the exception that detergent was omitted from the purification. After sequential washes with TBS (20 mM Tris-HCl at pH 7.4, 150 mM NaCl) containing 1 M NaCl and 0.1 M glycine at pH 4.5, TF protein was eluted from the column with 0.1 M glycine buffer at pH 2.5. The pH was adjusted to pH 6.0 or greater immediately upon elution and the eluted proteins were dialyzed against TBS for storage at −70C. This single-step purification yielded one major band of 40 kilodalton (kDa) and three minor bands under nonreducing conditions on an SDS-polyacrylamide gel. The secreted TF mutants were further purified by ion exchange chromatography on a MonoQ column (Pharmacia LKB, Piscataway, N.J.) as described by Ruf et al., *J. Cryst. Growth*, 122:253–264 (1992), the disclosure of which is hereby incorporated by reference. The truncated TF mutants lacked the ability to stably localize as a transmembrane cell surface protein, a property that was consistent with the removal of the predicted transmembrane domain to the carboxy terminus of amino acid residue position 219 in TF.

3. Characterization of Tissue Factor Mutants

A. Specific Functional Activity Assays

1) Coagulation Assays

The full-length TF mutants prepared above were analyzed for function by coagulation assay. For the assays described herein, the coagulation proteins were purified as described Ruf et al., *J. Biol. Chem.*, 266:2158–2166 (1991), the disclosure of which is hereby incorporated by reference. VIIa was purchased from Novo Nordisk (Gentofte, Denmark) and the functional activity and binding characteristics of the recombinant protein have previously been described by Ruf et al., *J. Biol. Chem.*, 266:15719–15725 (1991). Coagulation factor deficient plasmas were purchased from George King Bio-medical. The chromogenic substrate, Spectrozyme FXa, was from American Diagnostica Inc. (Greenwich, Conn.).

The concentration of mutant or control wild-type TF in the transfected CHO-cells was first determined by immunoassay by using two non-overlapping monoclonal antibodies. An alternative approach was to use a polyvalent antibody purified by affinity for capturing TF followed by detection with the TF8-5G9 monoclonal antibody described above.

The assay was performed as described by Ruf et al., *J. Biol. Chem.*, 266:2158–2166 (1991), the disclosure of which is hereby incorporated by reference. The assay was calibrated with recombinant wild-type human TF prepared as described for mutant TF in Examples 1 and 2. Initiation of coagulation by wild-type and mutant TF in recalcified plasma was determined after lysis of cell pellets from $2\times10^6$ cells/ml for each expressed full-length mutant with 15 mM octyl-glucopyranoside in HBS for 15 minutes at 37C. followed by a 3-fold dilution.

Clotting times were determined for the cell lysates in a one stage clotting assay containing equal volumes of sample, plasma, lysate and 20 mM $CaCl_2$ and converted to units based on a calibration curve established with purified TF reconstituted in phospholipid vesicles (70% phosphatidylcholine, 30% phosphatidylserine) using detergent solubilization and dialysis, as described in detail by Ruf et al., *Thrombosis and Haemostasis*, 66:529–533 (1991). The coefficient of variation calculated for a one month sampling period was 10.1% (n=6) for the ELISA and 10.8% (n=16) for the clotting assay.

Coagulant activity was normalized based on the antigen concentration to yield the specific activities for mutant and wild-type TF. Loss of specific function was calculated relative to transfected and expressed wild-type TF. All data represented are based on at least three independent determinations performed in duplicate.

Figure 2A:
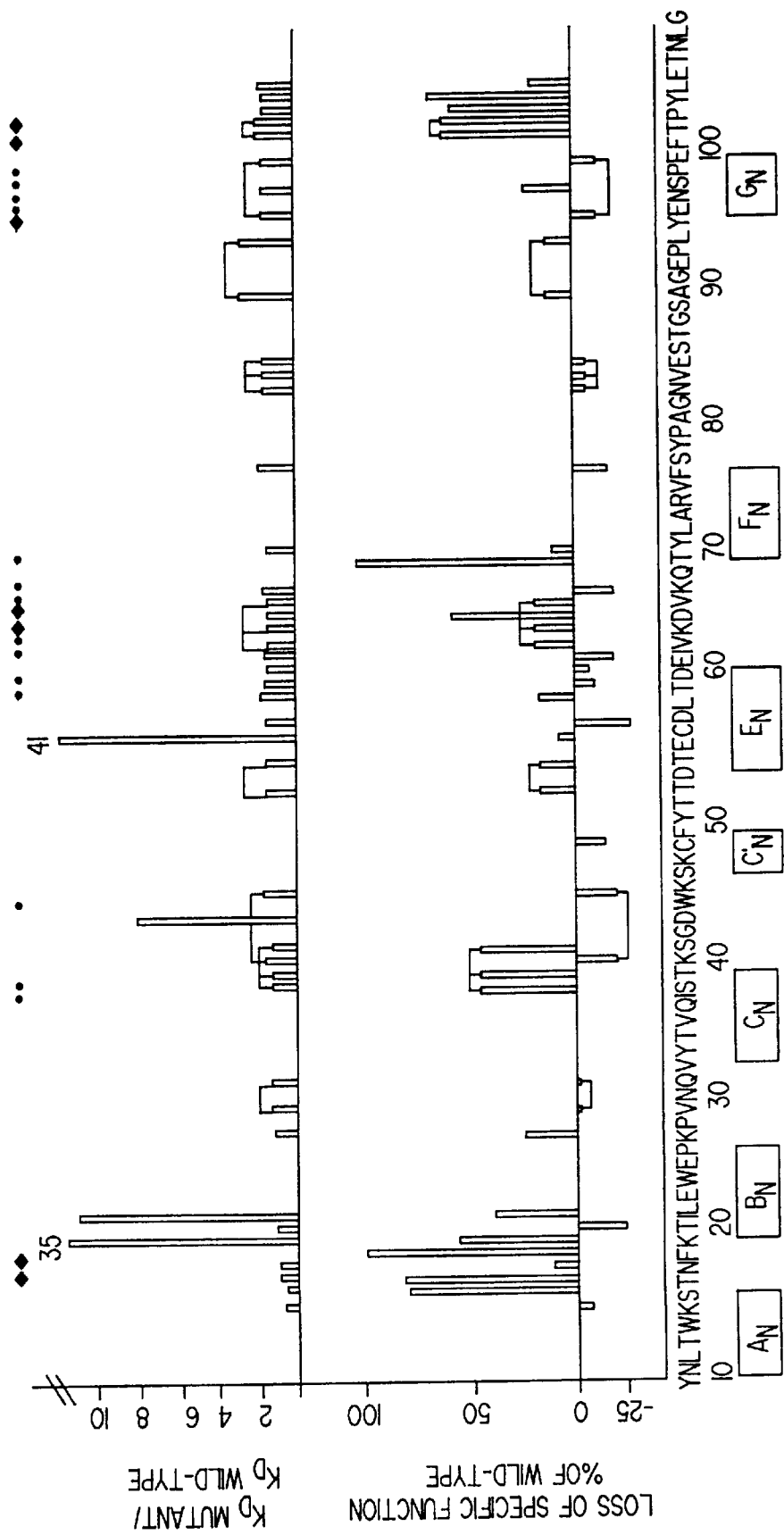
FIGS. 2A and 2B illustrate the functional characterization of site-directed Ala replacements for residues in TF. Mutants in the amino acid residue sequence 10–109 (FIG. 2A) and 110–210 (FIG. 2B) are aligned with predicted β-strands (boxes below the sequence) which are based on the alignment of the TF sequence with the GHR structure. Linked bars indicate multiple Ala substitutions in a single mutant. The lower panel of the graphs in FIGS. 2A and 2B depicts the reduction in specific functional activity as % of wild-type activity (100%—(specific activity mutant/specific activity wild-type) %). The upper panel depicts the change in apparent $K_D$ (ratio of $K_D$ mutant/$K_D$ wild-type). The symbols aligned on top of the upper graph mark the positions that are part of either of the two desolvated ligand interfaces in the GHR; diamonds indicate residues which form hydrogen bonds or salt bridges. The shaded area indicates a functional region in TF which mediates interaction with macromolecular substrates.
Figure 2B:
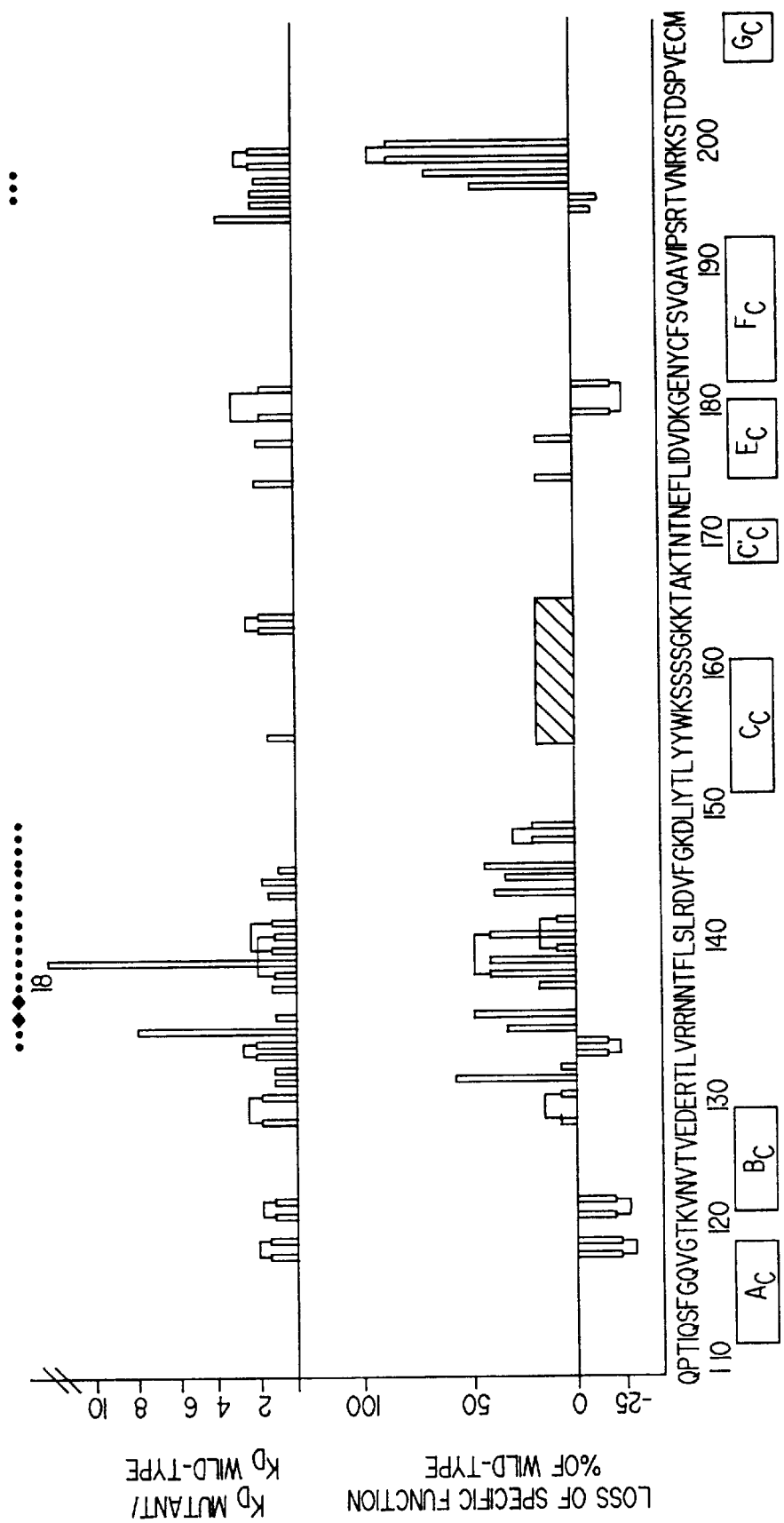

The results of the TF mutant protein functional determinations as measured by coagulation are shown in FIG. 2. TF mutants having alanine substitutions in the amino acid residue sequence 10–109 (FIG. 2A) and 110–210 (FIG. 2B) are aligned with predicted β-strands (boxes below the sequence) which are based on the alignment of the TF sequence with the GHR structure. Linked bars indicate multiple Ala substitutions in a single mutant. The lower panel of the graphs in FIGS. 2A and 2B depicts the reduction in specific functional activity as % of wild-type activity (100%—(specific activity mutant/specific activity wild-type) %). The upper panel depicts the change in apparent $K_D$ (ratio of $K_D$ mutant/$K_D$ wild-type) which is described below in Example 3A2) as determined in the chromogenic assay. The symbols aligned on top of the upper graph mark the positions that are part of either of the two desolvated ligand interfaces in the GHR; diamonds indicate residues which form hydrogen bonds or salt bridges. The shaded area indicates a functional region in TF which mediates interaction with macromolecular substrates.

The mutants of human TF were expressed as full length transmembrane proteins in mammalian cells with analysis of expression levels by immunoassay as described in Example 2B and of function by coagulation assay. Replacement of residues Ser-16, Thr-17, or Phe-19 in the loop connecting the $A_N$- and $B_N$-strands reduced function by more than 70%, while 55% and 35% respective losses of function were observed for the Lys-20 to Ala and the Ile-22 to Ala exchanges in β-strand BN as shown in FIG. 2A, in the lower panel. In the $C_N$-$C'_N$-loop, combined replacement of Ser-39-Thr-40-Ser-42 (S39-T40-S42) with alanines and prepared in a single mutant as described in Example 1B reproducibly decreased function by 43%, indicating that at least one of these residues modestly contributed to function. mhuTF mutants designated S16-T17-K20 and K65-D66-K68 similarly prepared as described in Example 1B exhibited decreased function by 98 and 70%, respectively, but were also observed to not substantially bind Factor VIIIa, and therefore, were not studied further.

In strands $E_N$ and $F_N$ and their connecting loop, exchanges of Val-67 or Tyr-71 resulted in 53% and 98% losses of function, respectively. In the peptide sequence connecting the two structural modules, Ala replacement for Tyr-103/ Leu-104, Glu-105, or Thr-106 reduced function more than 50%. A functional region in the carboxyl module was localized to the $B_C$–$C_C$-loop, based on 30–50% reductions in function upon exchange of Arg-131, Arg-135, Arg-136, Thr-139/Ser-142, Phe-140, Asp-145, Val-146, or Phe-147 as shown in the lower panel of FIG. 2B. Replacement of Val-198, Asn-199, or Arg-200/Lys-201 in the $F_C$–$G_C$-loop reduced function 30–80% (FIG. 2B). Additional studies of Asp-44 (not shown in FIG. 2) indicate that alanine substitutions resulted in an 85% loss of specific functional activity (Vmax) compared to wt-TF. Mutational exchange of the other residues shown in FIGS. 2A and 2B resulted in less than 25% losses of function. These data are consistent with a recognition site formed by residues discontinuous in linear sequence localized in several loops connecting β-strands, as well as in certain β-strands adjacent to these loops.

2) Chromogenic Assays

To further analyze the binding of VIIa to wild-type and mutant TF proteins expressed in Example 2, a linked chromogenic assay with purified VIIa and factor X was used. Cell lysates were prepared from CHO cell pellets in which full-length wild-type or mutant TF proteins were expressed as described in Example 1 and 2. The lysate was prepared by treating cell pellets with 15 mM octyl-glucopyranoside for 15 minutes at 37C. followed by a 3-fold dilution. The TF proteins were then purified and assembled at a concentration of 1 to 6 picomolar (pM)) with recombinant VIIa (0.5 pM to 15 nM) at 5 mM $Ca^{2+}$ for 10 minutes followed by addition of Factor X (100 nM). Maximum functional activity of the TF-VIIa complex was obtained in less than 3 minutes of assay time suggesting that equilibrium was approximated. Formed TF-VIIa complexes were quantified with substrate factor X added at 100 nM for a fixed time. Samples were then removed from the reaction and quenched in 100 mM EDTA in TBS (20 mM Tris-HCl, 140 mM NaCl, pH 7.4). The formation of Xa in the quenched reaction was determined with the chromogenic peptidyl substrate, Spectrozyme FXa (1.2 mM). The rate of Spectrozyme hydrolysis, measured as the increase in absorbance (mOD/min), was determined at ambient temperature in a kinetic plate reader (Molecular Devices, Mountain View, Calif.) followed by quenching and monitoring of product factor Xa formation using the Spectrozyme FXa.

Increasing or decreasing the time period for the activation of factor X by 2-fold did not influence the apparent dissociation constant ($K_{Dapp}$) determination, suggesting that the equilibrium of the TF-VIIa complex did not change slowly following the addition of substrate. Further, increasing or decreasing the factor X concentration 4-fold did not result in detectable changes of the $K_{Dapp}$, indicating that substrate was not limiting and that the substrate factor X did not influence the $K_{Dapp}$ determination. Enzfitter (Elsevier Biosoft) programs were employed to calculate the $K_{Dapp}$ from the experimentally determined bound VIIa, and free VIIa which was obtained by subtracting bound VIIa from the initial VIIa concentration. The calculated $K_{Dapp}$ for mutant TF proteins represent the means from at least three independent determinations with coefficients of variation <25%. The $K_{Dapp}$ for wild-type TF was 4.1±1.0 pM (mean±standard deviation, n=16). This $K_{Dapp}$ is similar to $K_D$ determinations at equilibrium with active site modified VIIa as shown by Waxman et al., *Biochem.*, 31:3998–4003 (1992).

The interaction of the ligand VIIa with the TF mutants as measured by the apparent dissociation constants ($K_{Dapp}$) in a functional assay are shown in the upper panels of FIGS. 2A and 2B. The data is plotted as the change in apparent $K_D$ (ratio of $K_D$ mutant/$K_D$ wild-type). The Lys-20 to Ala and Ile-22 to Ala mutants exhibited 35- and 11-fold increases, respectively, in the $K_{Dapp}$ for the TF-VIIa interaction compared to wild-type TF. The $K_{Dapp}$ was not changed upon exchanges in the $C_N$-$C'_N$- or the $E_N$-$F_N$-loop; however, the Asp-58 to Ala exchange ($E_N$-strand) increased the $K_{Dapp}$ 41-fold. The single Tyr-71 to Ala exchange could not be evaluated due to low expression levels, but the $K_{Dapp}$ was found to be increased 2.1-fold for the Val-64/Tyr-71 to Ala double mutant, consistent with only a minor contribution of Tyr-71 to the binding energy. Similarly, Ala exchanges of residues in the sequence connecting the two structural modules resulted in less than 2-fold changes in the $K_{Dapp}$. In the carboxyl module as shown in the upper panel of FIG. 2B, Arg-135 or Phe-140 substitutions by Ala ($B_C$-$C_C$-loop) increased the $K_{Dapp}$ 7.4- and 18-fold, respectively. The Arg-196 replacement in the $F_C$-$G_C$-loop resulted in a 3.5-fold increased $K_{Dapp}$.

The functional activity determined by the coagulation assays as described in Example 3A1) was not strictly correlated with changes in the $K_{Dapp}$ as shown herein. However, such a correlation is not necessarily expected, because the $K_{Dapp}$ was evaluated at concentrations of VIIa which are several orders of magnitude lower than the plasma concentration of VII. Consequently, considerable changes in the $K_{Dapp}$ may not result in equivalent losses of clotting function. Furthermore, function determined by coagulation assay is dependent on the kinetics of assembly of the cofactor-enzyme complex and this effect is minimized in the $K_{Dapp}$ determination by a preincubation step in. the analytical procedure. Since residues may contribute differently to the assembly and the dissociation of the TF-VIIa complex, mutation of certain residues may predominantly result in loss of coagulant function rather than changing the $K_{Dapp}$. Both the residues which contribute to the affinity of the TF-VIIa interaction and the residues which demonstrated marked losses of specific coagulant function upon mutational exchange were localized to the same regions of TF as shown in FIG. 2. With the exception of the sequence connecting the two structural modules, each of the regions proposed to be required for the assembly of VIIa was thus concordantly identified by both of the functional analyses.

Thus, amino acid residues that contributed to recognition of ligand have been identified predominantly at the boundary between the two structural modules as illustrated in FIG. 2. Ala replacement of all residues in the $C'_C$–$E_C$-loop at the inter-module boundary failed to identify residues critical for function as previously described by Ruf et al., *J. Biol. Chem.*, 267:22206–22210 (1992), the disclosure of which is hereby incorporated by reference. Moreover, surface loops oriented away from the inter-module boundary, such as the $B_N$-$C_N$, $C'_N$-$E_N$-, $F_N$-$G_N$-, $A_C$-$B_C$-, or $E_C$-$F_C$-loops readily tolerated Ala exchanges. Functionally important residues of TF have previously been identified in the $C_C$-$C'_C$-loop which is oriented away from the inter-module region. However, both quantitative radioligand binding analysis to mutant TF and efficient competition for ligand binding between mutant and wild-type TF in a functional assay suggested that this region is not required for binding of ligand as described by Ruf et al., *J. Biol. Chem.*, 267:6375–6381 (1992). Accordingly, the $K_{Dapp}$ determined in the present analysis for mutants in the $C_C$-$C'_C$-loop was comparable to wild-type TF as shown in FIG. 2B, in the upper panel. These mutants were further indistinguishable from wild-type TF in their ability to promote the cleavage of peptidyl substrates by the bound ligand VIIa, but they lacked efficient activation of protein substrates. The evidence obtained for the $C_C$-$C'_C$-loop amino acid region from 150 to 170 is therefore consistent with its deduced role as an interactive site for a third molecule, i.e. macromolecular substrate factor X or IX, rather than to mediate high affinity binding of the ligand VIIa.

Additional mhuTF mutants were prepared based on amino acid residue substitutions at amino acid residue position number D44. Mutant mhuTF was prepared as described in Example 1B in which alanine (A), arginine (R), or glutamic acid (E) were substituted in place of D44. The resulting mutants were analyzed as described in Example 3 for the ability to bind factor VIIa, and the ability to functionally cleave Factor X. Whereas wild-type recombinant human TF exhibited a reaction rate (Vmax) of about 2.0 per second, A44, E44 and R44 exhibited reaction rates of about 0.3, 0.4, and 0.5, respectively, which rates indicate an 85%, 80%, and 75% loss of function, respectively, compared to wild-type. In addition, whereas wt-mhuTF exhibited a $K_D$ of about 3 picoMolar (pM), A44, E44 and R44 exhibited activities of about 43.0, 7.0, and 11.0, respectively.

Figure 1B:
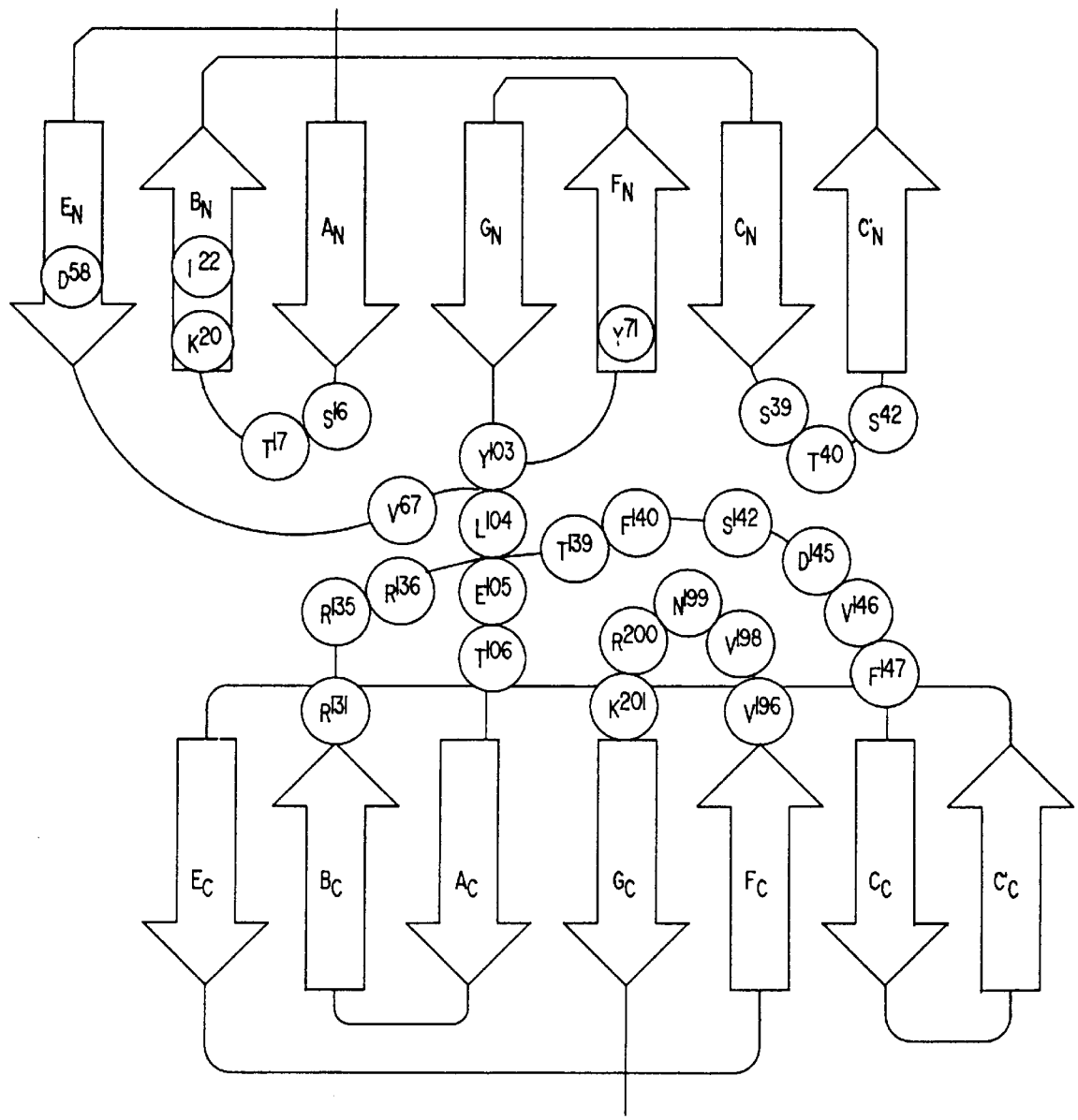

In summary, ligand VIIa interactive residues were found clustered at the boundary between the two structural modules of TF as shown in FIG. 1B. At least 25 residues were mutated in regions which appear to not be required for ligand recognition, and none of these mutants demonstrated loss of function. In contrast, at least 40% of the more than 50 mutated residues in the regions strongly implicated in ligand recognition were dysfunctional in one or both of the assays used.

The preferred TF mutants of this invention that exhibit binding to VIIa while demonstrating substantially reduced functional catalytic activity have alanine substitutions in the following amino acid residue positions: S16; T17; S39; T40; S42; D44; V67; L104; E105; T106; R131; R136; D145; V146; F147; V198; N199; R200 and K201. Other preferred mutants are those having the substitution E44 or R44. Based on this large number of mutants and the high frequency of dysfunctional mutants in the proposed ligand recognition site, the assignment of the functional and non-functional regions is therefore considered reasonable and concordant with data.

B. Western Blot Analysis of Mutant TF Proteins

Mutant and wild-type TF proteins expressed in mammalian cells were assessed by Western blot analysis of cell lysates prepared above after electrophoretic separation. For specific mutants as described below, this analysis revealed evidence for increased intracellular degradation and for changes in the glycosylation pattern relative to wild-type TF previously described by Rehemtulla et al., *J. Biol. Chem.*, 266:10294–10299 (1991) which were taken as indications of misfolded mutant proteins.

For all mutants, the indirect criteria of efficient cellular expression as well as glycosylation by the mammalian cells in a pattern typical for the control wild-type TF were adopted as evidence for the highly discriminating cellular recognition and processing of a properly folded protein. The severely dysfunctional mutants Phe-19 to Ala and Thr-60 to Ala as shown in FIG. 2A were expressed at low levels and, based on Western-blot analysis of cell lysates, exhibited significant fragmentation suggesting structural alterations leading to increased intracellular degradation. Due to its location in a loop at the inter-module boundary, Phe-19 may provide structurally important inter-module contacts analogous to the Arg-39 to Asp-132 salt bridge in the GHR as described by De Vos et al., *Science*, 255:306–312 (1992).

The Tyr-71 to Ala mutant was also poorly expressed, but appeared to be properly glycosylated without evidence of significant intracellular degradation, implying that the global folding of this mutant was unaltered. All other mutants were expressed at levels and with apparent alycosylation patterns comparable to control wild-type TF.

The reactivity of the mutants with monoclonal antibodies was also analyzed functionally as additional evidence for properly folded mutant proteins. Mutant or wild-type TF were incubated for 30 minutes with each of the inhibitory and conformation-dependent monoclonal antibodies (30 ug/ml) to three non-overlapping epitopes on TF described by Ruf et al., *Biochem. J.*, 278:729–733 (1991), the disclosure of which is hereby incorporated by reference. Quantitation of residual coagulant activity followed and was performed as described in Example 3A1) in comparison to a non-inhibited sample. Reduction in antibody inhibition by 10% compared to wild-type TF was considered evidence for loss of structure necessary for antibody reactivity.

C. Structural Analysis of Mutant TF Proteins

The indirect approaches to evaluate potential structural alterations were complemented by direct physicochemical analysis to ensure structural integrity of dysfunctional mutants in functionally important regions of both modules of TF. The isolated extracellular domains of wild-type and selected mutant TF proteins prepared in Example 2 were analyzed by circular dichroism and 600 MHz $^1$H nuclear magnetic resonance ($^1$H-NMR) spectroscopy. Circular dichroism spectra were generated on an Aviv 61DS spectropolarimeter at a protein concentration of approximately 20 uM in 50 mM NaCl, 2.5 mM phosphate, 50 uM EDTA at pH 7.0. $^1$H-NMR spectra were recorded on a Bruker AMX600 spectrometer with samples (50–200 uM) in $D_2O$, 50 mM NaCl, 2.5 mM phosphate, 50 uM EDTA at pH 7.0. The residual $H_2O$ resonance was suppressed by preirradiation.

Figure 3:
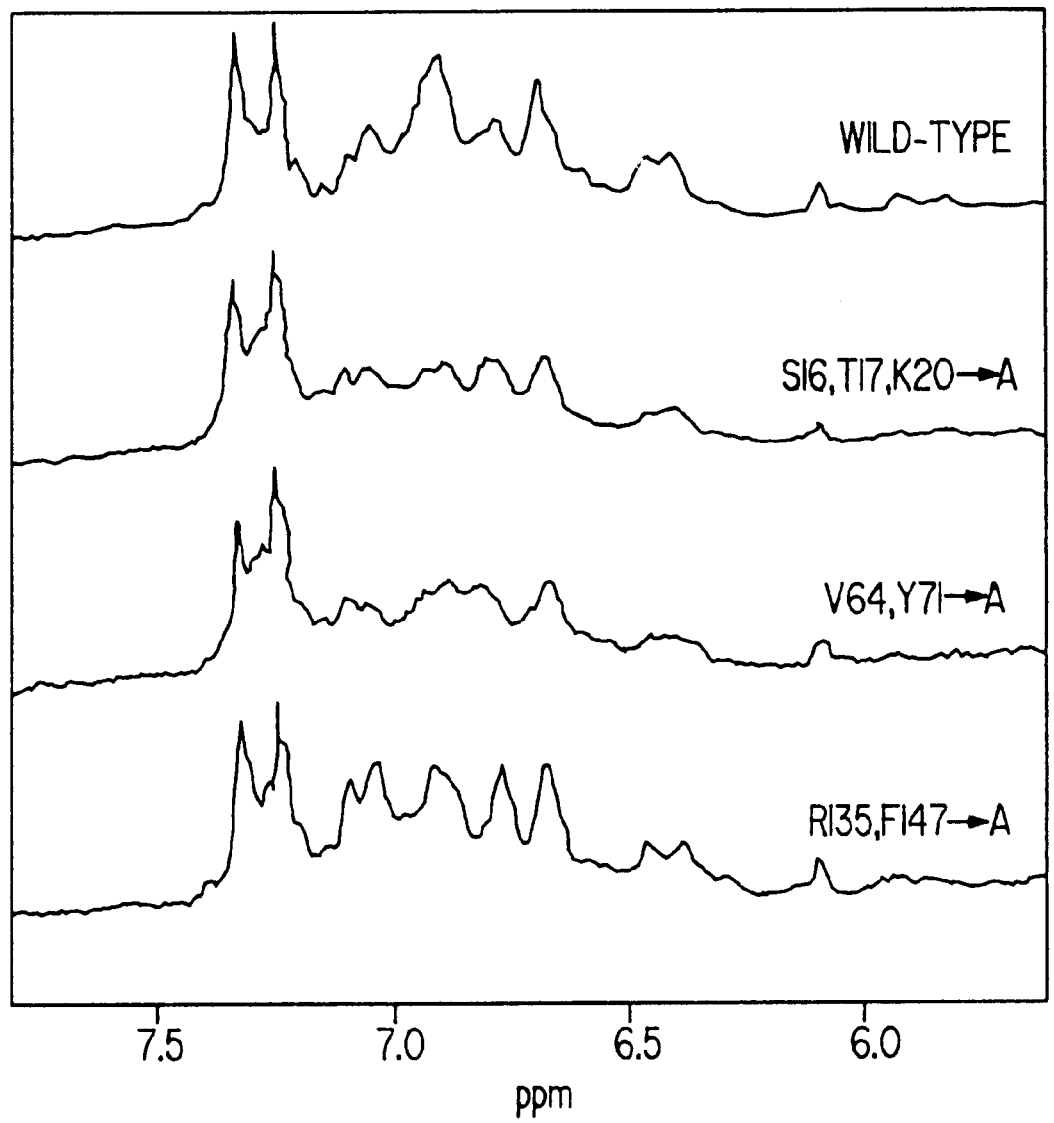
FIG. 3 illustrates the aromatic regions of the 600 MHz $^1$H-NMR spectra of selected TF mutants. The isolated and soluble TF extracellular domains (residues 1–218) of wild-type and mutant TF were expressed in yeast for structural analysis.

In order to increase the probability for identification of structural alterations, the structural integrity of the TF mutants with multiple amino acid substitutions were analyzed since they would exhibit a greater loss of specific function. The CD spectra and the NMR spectra, the latter of which is shown in FIG. 3, of mutants in three different functionally relevant regions exhibited features typical for wild-type TF. Based on these independent criteria, all but the Phe-19 and Thr-60 mutants adopted proper global folding. The diminished function can therefore be attributed to either subtle local conformational alterations in the ligand interface or to the removal of side chains directly contributing to interaction with ligand.

D. Comparison of TF with Growth Hormone and Cytokine Ligand Binding Interfaces

Amino acid residues in the extracellular domain of TF which are critical for binding of ligand and for function were identified by Ala replacement mutagenesis as shown in FIGS. 1 and 2. No single sequence span could be defined which solely mediated the interaction with VIIa. Rather, several residues discontinuous in linear sequence were found that contributed to the affinity of the TF-VIIa interaction and to coagulant function, consistent with other examples of protein interactive sites as described by Chothia et al., *J. Biol. Chem.*, 265:16027–16030 (1990).

Residues that contributed to binding of VIIa were found in both predicted structural modules of TF as shown in FIG. 1. Based on the structural model, functionally important residues were located in various loops and adjacent β-strands at the inter-module boundary. These residues may potentially form a contiguous protein surface area for ligand interaction. The ligand interface likely involves additional residues that are adjacent to these functionally important residues, but which have not been identified by the mutational analysis because they provide backbone rather than side chain interaction with ligand. Potentially, mutations of residues with side chain interactions could remain silent in functional analysis, as demonstrated for certain crystallographically defined contact residues of the growth hormone receptor as described by Gobius et al., *J. Mol. Endocrinol.*, 9:213–220 (1992).

Although mutating a single residue may not conclusively establish its contribution to a ligand interface, the global assignment of a functional site based on multiple amino acid substitutions is less ambiguous, because mutations in a protein interactive site generally result in some loss of function. In this invention, several residues were identified in TF which contribute to binding of VIIa, thus providing an assignment of the ligand interface on the basis of multiple amino acid replacements. Multiple amino acid exchanges in the regions oriented away from the proposed area for ligand recognition at the inter-module boundary were functionally silent, thus the overall mapping of the ligand site in TF is reliable. The TF mutants of this invention, both full-length and truncated forms and either singly or multiply mutated, can thus be used as antagonists of normal TF function as they will bind to VIIa without allowing the TF-mediated catalytic coagulant activity to occur as shown by the assays described herein.

The TF extracellular domain has been predicted to adopt the folding pattern of the cytokine receptor homology domain which consists of a pair of seven β-strand modules. Although additional protein modules are found in several of the cytokine receptors and their associated signal transducing molecules, it appears that ligand recognition is typically mediated by one homology module pair, as demonstrated for the murine interleukin-3 and the granulocyte colony-stimulating factor receptors as described respectively by Wang et al., *J. Biol. Chem.*, 267:979–983 (1992) and Fukunaga et al., *EMBO J.*, 10:2855–2865 (1991). The growth hormone receptor (GHR) extracellular domain consists entirely of the homology module pair. The residues that mediate ligand interaction have been defined by Ala scanning mutagenesis and the crystallographic solution of the GHR in complex with its ligand. See, De Vos et al., *Science*, 255:306–312 (1992) and Bass et al., *Proc. Natl. Acad. Sci., USA*, 88:4498–4502 (1991).

The residues that are implicated in ligand recognition by TF are localized within or in close proximity to areas corresponding to the GHR-ligand interface as shown in FIG. 1A and 1B. Specifically, two GHR residues which bridge to ligand are localized in the $A_N$-$B_N$-loop, and the closely related prolactin receptor employs the same site for ligand binding as described by Rozakis-Adcock et al., *J. Biol. Chem.*, 267:7428–7433 (1992). Several residues in this same region in TF contribute significantly to binding of ligand and function. Minor functional loss was observed for exchanges in the $C_N$-$C'_N$-loops of both TF and GHR as described by Bass et al., *Proc. Natl. Acad. Sci., USA*, 88:4498–4502 (1991). The residues most critical for binding of the ligand by GHR are localized to the $E_N$-$F_N$-loop region, and residues Asp-58, Val-67 and Tyr-71 in the corresponding region of TF support function and binding.

Several residues important for function of TF were identified in the sequence connecting the two structural modules. The corresponding GHR residues provide contacts with ligand as shown in FIG. 1. Residues critical for TF function are localized in the $B_C$-$C_C$-loop which is almost entirely buried in the interface of GHR with its ligand. The two contact residues in this region of the GHR align with Arg-135 and Arg-136 in TF which both contribute to interaction with ligand. Moreover, corresponding residues in two other members of the receptor family, the interleukin-2 receptor as described by Imler et al., *EMBO J.*, 11:2047–2053 (1992) and the murine interleukin-3 receptor as described by Wang et al., *J. Biol. Chem.*, 267:979–983 (1992), contribute to binding of ligand.

Amino acid residues Arg-196, Val-198, Asn-199, Arg-200 and Lys-201 in the $F_C$-$G_C$-loop of TF contribute to function and binding of ligand, whereas the corresponding ligand interface residues in GHR appear not to be required for ligand binding as described by De Vos et al., *Science*, 255:306–312 (1992). TF residue Lys-201 corresponds to the first Trp residuE in the highly conserved Trp-Ser-Xaa-Trp-Ser (SEQ ID NO 9) sequence motif found in most members of the cytokine receptor family. Although residues in this motif do not directly participate in the interaction of growth hormone with its receptor, mutations of this motif in the interleukin-2 receptor-chain as described by Miyazaki et al., *EMBO J.*, 10:3191–3197 (1991) or erythropoietin receptor as described by Yoshimura et al., *J. Biol. Chem.*, 267:11619–11625 (1992) result in structurally altered receptors and diminished affinity for ligand. Less disruptive mutations of the Trp-Ser-Xaa-Trp-Ser motif in the erythropoietin receptor further indicate a contribution of these residues to functional assembly required for signal transduction as described by Quelle et al., *Mol. Cell. Biol.*, 12:4553–4561 (1992), consistent with a functional role of residues in this motif in proximity to the ligand interface.

The discovery of a ligand interactive area in TF thus strongly suggests that the localization of the ligand interface is conserved to a large extent between the GHR and TF, a distant member of the cytokine receptor family as described by Bazan, *Proc. Natl. Acad. Sci., USA*, 87:6934–6938 (1990). The emerging, though limited, analysis of ligand recognition determinants in other receptors of the family is further consistent with the hypothesis that the ligand recognition interface formed by the two structural modules is architecturally conserved throughout the receptor family.

Molecular recognition through a tandem pair of structural modules may be more widely used in protein-protein interactions, as demonstrated by the suggested involvement of at least two adjacent type III repeats in fibronectin for interaction with integrins or by antigen recognition in the immunoglobulin family. Similar to immunoglobulin modules, the cytokine receptors appear to employ several surface loops to create structure with specificity for recognition of ligand. In immunoglobulins, the paired recognition of ligand is achieved by parallel alignment of light and heavy chains; thus, loops at the same pole in both modules are used for binding of ligand. In contrast, the cytokine receptor family employs tandem alignment of a similar structural framework. This results in recognition of ligand at the boundary between modules which contribute surface loops from opposite poles. Diversity in recognition of ligands may be generated by variability in the primary sequence and in the length of loops which form the ligand interface. In addition, the architecture of the recognition site will depend on the relative orientation of the two structural modules at the inter-module boundary.

In cytokine receptors, this type of ligand binding site appears to recognize helical ligands. Although very short helical stretches may be associated with the predominant β-structure of epidermal growth factor-like (EGF) domains as described by Hommel et al., *J. Mol. Biol.*, 227:271–283

(1992), recognition of a paired helical motif appears to be replaced by recognition of two EGF-modules in the case of TF as shown by Toomey et al., *J. Biol. Chem.,* 266:19198–19202 (1991). However, further complexity is introduced by the proposed contribution of protease domain residues in VIIa to the interaction with TF as described by O'Brien et al., *Blood,* 78:132–140 (1991). The complementary binding site in VIIa may thus be formed by residues in different structural modules associated to form a contiguous interactive site. Although built from protein modules with structural scaffolds different from the helical cytokines, the interactive site in VIIa may potentially share some of the structural characteristics of the receptor interface of cytokine ligands.

The structural elucidation of the TF-VIIa interface of this invention and the comparison with ligand interfaces of other members of the cytokine receptor family promises to provide more general rules for how the structural scaffold of two β-strand modules allows both diversity and specificity of ligand recognition. The mutant TF proteins of this invention that provided the basis for the determination of the ligand interface are valuable therapeutic compositions in that they bind to VIIa without allowing the formed TF-VIIa complex to catalyze inactive coagulant proteins. Thus, in a therapeutic setting, the mutant TF proteins ameliorate any acute disease attributable to excessive activation of coagulation by TF, such as disseminated vascular occlusion, acute thrombosis associated with malignancy, transient ischemic attacks, and the like.

4. Reconstitution of Purified Tissue Factor Mutants with Phospholilid

A. Preparation of Phospholipids

For use in the therapeutic aspects of this invention, the full-length TF mutants prepared in Example 2 are reconstituted with phospholipid as described herein. Phosphatidylcholine (PC), phosphatidylethanolamine (PE), phosphatidylserine (FS) and phosphatidylglycerol (PG) are obtained in chloroform solution from Avanti Polar Lipids in Alabaster, Ala., or Calbiochem Corporation in La Jolla, Calif., in sealed glass ampules and stored under $N_2$ at −20C. CHAPS, other detergents and bovine gamma globulin are obtained from Calbiochem. Tris base and glycine are purchased from Bio-Rad Laboratories in Richmond, Calif. All other chemicals and biochemicals are acquired from Sigma in St. Louis, Mo.

Phospholipids are prepared for resolubilization in the following manner. PC, PE, PS, and PG are warmed to room temperature and combined in a suitable tube or flask at the specified mole ratios. The antioxidant, butyrated hydroxytoluene (BHT), is dissolved in chloroform and added to the mixture of phospholipids at a weight ratio of 0.1% (BHT:total phospholipids). Organic solvent is removed by evaporation under a stream of dry nitrogen or under reduced pressure in a rotary evaporator. Residual organic solvent is eliminated by pumping an additional 1 hour at room temperature with a vacuum pump at a pressure of 10 μm or less. The mixture of phospholipids is redissolved to 20 mg/ml in 20 mM Tris-HCl at pH 7.5, 150 mM NaCl (TES) containing 100 mM CHAPS (3-[(3-cholamidopropyl)-dimethylammonio]-1-propanesulfonate).

The full-length TF mutants prepared in Example 2 are then separately admixed with carrier protein and are then combined with the redissolved phospholipids prepared above. The volume of the resulting mixture is adjusted with a buffer as described above, preferably containing cryopreservative (most preferably trehalose) and glycine but without extra added detergent. Various permutations for the preparation of phospholipid-mutant TF reagents of this invention are presented below.

B. Preparation of the Mutant TF/Phospholipid (mhuTF/P) Reagents by Dialysis

Phospholipids are combined at the specified mole ratios of PC, PE, PS, and PG, then resolubilized as described above. The resolubilized phospholipids are combined with the mutant TF proteins of this invention and bovine gamma globulin. Additional TBS containing 150 mM trehalose is added to yield final concentrations of 4 mg/ml total phospholipid, 10 μg/ml of each mutant TF protein, 1 mg/ml bovine gamma globulin and 20 mM CHAPS. This clear and colorless solution is placed in a dialysis membrane tubing (Spectrapore®, Spectrum Medical Industries, molecular weight cutoff of 12,000 to 14,000) and dialyzed for at least 30 hours at room temperature against TBS containing 150 mM trehalose and 0.05% $NaN_3$. After dialysis the volume of the dialysate is determined and adjusted back to the original volume, if required, with dialysis buffer. $CdCl_2$ is added to a final concentration of 5 mM and the solution is incubated at 37C. for 2 hours.

The solution is frozen on dry ice, then lyophilized using a cycle beginning at −40C. and ending at room temperature, over a 48 hour period. The liposomes are then reconstituted to a working concentration with 0.1 M Tris-HCl at pH 7.5, 150 mM trehalose to yield a solution containing a mutant TF at approximately 1 to 2 μg/ml, phospholipids at approximately 400 to 800 μg/ml, and bovine gamma globulin at 50 to 100 μg/ml.

C. Preparation of Preparation of the Mutant TF/Phospholipid (mhuTF/P) Reagents Without Dialysis Phospholipids are prepared for resolubilization in the following manner. PC, PE, and PS are warmed to room temperature and combined in a suitable tube or flask at a mole ratio of 7.5:1:1 of PC, PE, and PS, respectively. The antioxidant, butyrated hydroxytoluene (BHT), is dissolved in chloroform and added to the mixture of phospholipids at a weight ratio of 0.1% (BHT:total phospholipids). Organic solvent is removed by evaporation under a stream of dry nitrogen or under reduced pressure in a rotary evaporator. Residual organic solvent is eliminated by pumping an additional 1 hour at room temperature with a vacuum pump at a pressure of 10 μm or less.

The mixture of phospholipids is redissolved in 50 mM octyl beta-D-thioglucopyranoside (OTG) in 20 mM HEPES (pH 6), 150 mM NaCl to a final concentration of 4 mg/ml. The full-length mutant TF (mTF) proteins from Example 2 and bovine gamma globulin are mixed with the resolubilized phospholipids. Enough 20 mM HEPES.(pH 6), 150 mM NaCl is added to adjust the final concentrations to 10 μg/ml mTF, 1 mg/ml bovine gamma globulin, 4 mg/ml phospholipids, and 10 mM OTG. $CdCl_2$ is added to a final concentration of 5 mM to activate the mTF. The resulting mixed micelles comprised of mTF, OTG, and phospholipids are diluted with 20 mM HEPES, pH 6, 150 mM NaCl to yield a solution containing mTF at approximately 0.5 to 1 μg/ml, phospholipids at approximately 500 to 700 μg/ml, and bovine gamma globulin at 25 to 50 μg/ml to give mTF PT reagent.

D. Preparation of Mutant TF/Phospholipid (mhuTF/P) Reagent by Diafiltration

Phospholipids are combined at mole ratio of 7.5:1:1 (PC:PE:PS), dried to remove organic solvent, then resolubilized as described above. The resolubilized phospholipids at 15 mg/ml in TBS containing 100 mM CHAPS are combined with mutant TF proteins prepared in Example 2 and bovine gamma globulin. Additional TBS containing 150 mM trehalose is added to yield final concentrations of 4 mg/ml phospholipid, 10 μg/ml mTF, 1 mg/ml bovine gamma globulin and 20 mM CHAPS.

The detergent (CHAPS) is removed by tangential flow diafiltration using, a Pyrostart or Ultrastart filter unit (Sartorius Corp., Bohemia. N.Y., molecular weight cutoff of 20,000) and TBS containing 150 mM trehalose as the dialysis buffer. Approximately 95 to 100% of the CHAPS can be removed by passing 10 volumes of dialysis buffer through the device. After diafiltration the volume of the dialysate is determined and adjusted back to the original volume (if required) with TBS containing 150 mM trehalose and 0.05% $NaN_3$. $CdCl_2$ is added to a final concentration of 5 mM and the solution is incubated at 37C. for 2 hours.

The solution may be frozen on dry ice, then lyophilized using a cycle beginning at -40C. and ending at room temperature, over a 48 hour period. The resulting reagent may be reconstituted to working concentration with the addition of 0.1 M Tris-HCl at pH 7.5, 150 mM trehalose to yield a solution containing mhuTF at approximately 1 to 2 μg/ml, phospholipids at approximately 400 to 800 μg/ml, and bovine gamma globulin at 50 to 100 μg/ml.

E. Preparation of Mutant TF/Phospholipid (mhuTF/P) Reagent by Addition of XAD-2 Resin Phospholipids are combined at mole ratio of 67:16:10:7 (PC:PG:PE:PS), dried to remove organic solvent, then resolubilized as described above. The resolubilized phospholipids at 15 mg/ml in TBS containing 100 mM CHAPS and 0.8% glycine are combined with the full-length mutant TF proteins prepared in Example 2 and bovine gamma globulin. Additional TBS containing 150 mM trehalose and 0.8% glycine is added to yield final concentrations of 3 mg/ml phospholipid, 4.5 μg/ml mTF, 1 mg/ml bovine gamma globulin and 20 mM CHAPS.

Hydrophobic chromatographic resins such as Amberlite XAD-2 (Rohm and Haas Co., Philadelphia, Pa.) or Bio-Beads SM-2 (BioRad, Richmond, Calif.) can also be used to remove the detergent (CHAPS), either in direct contact with the phospholipid solution or separated from it by a dialysis membrane. The rate of removal is proportional to the weight ratio of the detergent in solution and the chromatographic resin beads. Indeed, the rate of removal is proportional to both the amount of resin added and the rate of addition. The amount required to remove all of the detergent is calculated from the capacity of the resin (provided by the manufacturer) and the total mass of detergent to be removed. Moreover, 99.9% removal of the detergent may be achieved either in 1 hour or in 24 hours, at 30C. depending upon the rate at which this amount of resin is added. $CdCl_2$ is added to a final concentration of 5 mM and the solution is incubated at 37C. for 2 hours. The liposomes are then diluted to a working concentration with 50 mM Tris-HCl at pH 7.5, 75 mM trehalose, 15 mM $CaCl_2$, 0.8% glycine, 1% maltose, and 0.05% $NaN_3$ to yield a solution containing mhuTF at approximately 0.04 to 0.20 μg/ml, phospholipids at approximately 40 to 150 μg/ml, and bovine gamma globulin at 50 to 100 μg/ml.

The solution is frozen on dry ice, then lyophilized using a cycle beginning at -40C. and ending at room temperature, over a 48 hour period. The lyophilized reagent is reconstituted with distilled water prior to use.

Following the above preparations, the resultant phospholipid-reconstituted full-length TF mutants of this invention can then be used in various therapeutic modalities to inhibit coagulation.

The foregoing specification, including the specific embodiments and examples, is intended to be illustrative of the present invention and is not to be taken as limiting. Numerous other variations and modifications can be effected without departing from the true spirit and scope of the present invention.

What is claimed is:

1. A mutant human tissue factor protein having the capacity to bind Factor VII/VIIa and having at least a 40 percent reduced tissue factor procoagulant cofactor activity, wherein said protein comprises the amino acid residue sequence shown in SEQ ID NO:2 from residues 1–218 and includes at least one selected semi-conservative amino acid residue substitution selected from the group consisting of G16, V17, G39, V40, G42, S44, G44, G67, S104, I104, S105, N105, G105, V106, S131, Q131, S136, Q136, S145, G145, G146, L147, I147, G198, S199, G199, T199, S200, Q200, S201, T201, N201.

2. The mutant human tissue factor protein of claim 1 wherein said protein has at least a 75 percent reduced tissue factor procoagulant cofactor activity.

3. The mutant human tissue factor protein of claim 2 wherein said substitution is selected from the group consisting of G16, V17, S44, G44, S199, G199, T199, S200, and Q200.

4. The mutant human tissue factor protein of claim 1 wherein said substitution is the group of three substitutions G39, V40, and G42.

5. The mutant human tissue factor protein of claim 1 wherein said protein is a soluble protein which lacks a membrane anchor shown in SEQ ID NO 2 at residues 219–263.

6. The mutant human tissue factor protein of claim 1 wherein said protein is a membrane-associated protein including a membrane anchor as shown in SEQ ID NO 2 from residues 219–263.

7. A therapeutic composition for inhibiting human tissue factor (huTF) comprising a pharmaceutically acceptable carrier and a therapeutic amount of a mutant human tissue factor protein according to claim 1.

8. The composition of claim 7 wherein said mhuTF protein is a membrane-associated protein including a membrane anchor and said composition further comprising liposomes.

9. The composition of claim 7 further comprising a carbohydrate cryopreservative selected from a group consisting of trehalose, maltose, lactose, glucose, and mannitol.

10. The composition of claim 7 further comprising a detergent.

11. The composition of claim 10 wherein said detergent is selected from the group consisting of octyl beta-D-glucopyranoside and octyl beta-D-thioglucopyranoside.

12. A method for inhibiting human tissue factor procoagulant activity associated with Factor VII/VIIa comprising contacting said Factor VII/VIIa with a mutant human tissue factor protein according to claim 1 in an amount sufficient to inhibit the procoagulant activity of said Factor VII/VIIa.

13. The method of claim 12 wherein said Factor VII/VIIa is present in a sample and said contacting is conducted by admixing said mutant human tissue factor protein with said sample.

14. The method of claim 12 wherein said Factor VII/VIIa is present in a body fluid of a human patient and said contacting is conducted by administering said mutant human tissue factor protein to said body fluid of said patient.

15. The method of claim 12 wherein said amount is an amount sufficient to subject said Factor VII/VIIa to from about 1 picomolar to about 100 nanomolar mutant human tissue factor protein.

* * * * *

SEQUENCE LISTING

```
(1) GENERAL INFORMATION:

(iii) NUMBER OF SEQUENCES: 9

(2) INFORMATION FOR SEQ ID NO:1:

(i) SEQUENCE CHARACTERISTICS:
         (A) LENGTH: 5437 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (ix) FEATURE:
         (A) NAME/KEY: sig_peptide
         (B) LOCATION: 2267..2362

(ix) FEATURE:
         (A) NAME/KEY: CDS
         (B) LOCATION: 2363..3154

(xi) SEQUENCE DESCRIPTION: SEQ ID NO:1:

GGCGTAATCT GCTGCTTGCA AACAAAAAAA CCACCGCTAC CAGCGGTGGT TTGTTTGCCG      60
```

| | |
|---|---|
| GATCAAGAGC TACCAACTCT TTTTCCGAAG GTAACTGGCT TCAGCAGAGC GCAGATACCA | 120 |
| AATACTGTCC TTCTAGTGTA GCCGTAGTTA GGCCACCACT TCAAGAACTC TGTAGCACCG | 180 |
| CCTACATACC TCGCTCTGCT AATCCTGTTA CCAGTGGCTG CTGCCAGTGG CGATAAGTCG | 240 |
| TGTCTTACCG GGTTGGACTC AAGACGATAG TTACCGGATA AGGCGCAGCG GTCGGGCTGA | 300 |
| ACGGGGGGTT CGTGCACAGA GCCCAGCTTG GAGCGAACGA CCTACACCGA ACTGAGATAC | 360 |
| CTACAGCGTG AGCATTGAGA AAGCGCCACG CTTCCCGAAG GGAGAAAGGC GGACAGGTAT | 420 |
| CCGGTAAGCG GCAGGGTCGG AACAGGAGAG CGCACGAGGG AGCTTCCAGG GGGAAACGCC | 480 |
| TGCTATCTTT ATGATCCTGT CGGGTTTCGC CACCTCTGAC TTGAGCGTCG ATTTTTGTGA | 540 |
| TGCTCGTCAG GGGGCGGAG CCTATGGAAA AACGCCAGCA ACGCAAGCTA GCTTCTAGCT | 600 |
| AGAAATTGTA AACGTTAATA TTTTGTTAAA ATTCGCGTTA AATTTTTGTT AAATCAGCTC | 660 |
| ATTTTTTAAC CAATAGGCCG AAATCGGCAA ATCCCTTAT AAATCAAAAG AATAGCCCGA | 720 |
| GATAGGGTTG AGTGTTGTTC CAGTTTGGAA CAAGAGTCCA CTATTAAAGA ACGTGGACTC | 780 |
| CAACGTCAAA GGGCGAAAAA CCGTCTATCA GGGCGATGGC CGCCCACTAC GTGAACCATC | 840 |
| ACCCAAATCA AGTTTTTTGG GGTCGAGGTG CCGTAAAGCA CTAAATCGGA ACCCTAAAGG | 900 |
| GAGCCCCCGA TTTAGAGCTT GACGGGGAAA GCCGGCGAAC GTGGCGAGAA AGGAAGGGAA | 960 |
| GAAAGCGAAA GGAGCGGGCG CTAGGGCGCT GGCAAGTGTA GCGGTCACGC TGCGCGTAAC | 1020 |
| CACCACACCC GCCGCGCTTA ATGCGCCGCT ACAGGGCGCG TACTATGGTT GCTTTGACGA | 1080 |
| GACCGTATAA CGTGCTTTCC TCGTTGGAAT CAGAGCGGGA GCTAAACAGG AGGCCGATTA | 1140 |
| AAGGGATTTT AGACAGGAAC GGTACGCCAG CTGGATCACC GCGGTCTTTC TCAACGTAAC | 1200 |
| ACTTTACAGC GGCGCGTCAT TTGATATGAT GCGCCCCGCT TCCCGATAAG GGAGCAGGCC | 1260 |
| AGTAAAAGCA TTACCCGTGG TGGGGTTCCC GAGCGGCCAA AGGGAGCAGA CTCTAAATCT | 1320 |
| GCCGTCATCG ACTTCGAAGG TTCGAATCCT TCCCCCACCA CCATCACTTT CAAAAGTCCG | 1380 |
| AAAGAATCTG CTCCCTGCTT GTGTGTTGGA GGTCGCTGAG TAGTGCGCGA GTAAAATTTA | 1440 |
| AGCTACAACA AGGCAAGGCT TGACCGACAA TTGCATGAAG AATCTGCTTA GGGTTAGGCG | 1500 |
| TTTTGCGCTG CTTCGCGATG TACGGGCCAG ATATACGCGT TGACATTGAT TATTGACTAG | 1560 |
| TTATTAATAG TAATCAATTA CGGGGTCATT AGTTCATAGC CCATATATGG AGTTCCGCGT | 1620 |
| TACATAACTT ACGGTAAATG GCCCGCCTGG CTGACCGCCC AACGACCCCC GCCCATTGAC | 1680 |
| GTCAATAATG ACGTATGTTC CCATAGTAAC GCCAATAGGG ACTTTCCATT GACGTCAATG | 1740 |
| GGTGGACTAT TTACGGTAAA CTGCCCACTT GGCAGTACAT CAAGTGTATC ATATGCCAAG | 1800 |
| TACGCCCCCT ATTGACGTCA ATGACGGTAA ATGGCCCGCC TGGCATTATG CCCAGTACAT | 1860 |
| GACCTTATGG GACTTTCCTA CTTGGCAGTA CATCTACGTA TTAGTCATCG CTATTACCAT | 1920 |
| GGTGATGCGG TTTTGGCAGT ACATCAATGG GCGTGGATAG CGGTTTGACT CACGGGGATT | 1980 |
| TCCAAGTCTC CACCCCATTG ACGTCAATGG GAGTTTGTTT TGGCACCAAA ATCAACGGGA | 2040 |
| CTTTCCAAAA TGTCGTAACA ACTCCGCCCC ATTGACGCAA ATGGGCGGTA GGCGTGTACG | 2100 |
| GTGGGAGGTC TATATAAGCA GAGCTCTCTG GCTAACTAGA GAACCCACTG CTTAACTGGC | 2160 |
| TTATCGAAAT TAATACGACT CACTATAGGG AGACCGGAAG CTTCTAGAGA TCCCTCGACC | 2220 |
| TCGATCCGAA TTCCGTTCCG CTCGATCTCG CCGCCAACTG GTAGACATGG AGACCCCTGC | 2280 |
| CTGGCCCCGG GTCCCGCGCC CCGAGACCGC CGTCGCTCGG ACGCTCCTGC TCGGCTGGGT | 2340 |
| CTTCGCCCAG GTGGCCGGCG CT TCA GGC ACT ACA AAT ACT GTG GCA GCA TAT | 2392 |
|   Ser Gly Thr Thr Asn Thr Val Ala Ala Tyr | |
|   1         5              10 | |

| | | |
|---|---|---|
| AAT TTA ACT TGG AAA TCA ACT AAT TTC AAG ACA ATT TTG GAG TGG GAA | 2440 |
| Asn Leu Thr Trp Lys Ser Thr Asn Phe Lys Thr Ile Leu Glu Trp Glu | |
|       15                  20                  25           | |

```
AAT TTA ACT TGG AAA TCA ACT AAT TTC AAG ACA ATT TTG GAG TGG GAA      2440
Asn Leu Thr Trp Lys Ser Thr Asn Phe Lys Thr Ile Leu Glu Trp Glu
            15                  20                  25

CCC AAA CCC GTC AAT CAA GTC TAC ACT GTT CAA ATA AGC ACT AAG TCA      2488
Pro Lys Pro Val Asn Gln Val Tyr Thr Val Gln Ile Ser Thr Lys Ser
            30                  35                  40

GGA GAT TGG AAA AGC AAA TGC TTT TAC ACA ACA GAC ACA GAG TGT GAC      2536
Gly Asp Trp Lys Ser Lys Cys Phe Tyr Thr Thr Asp Thr Glu Cys Asp
            45                  50                  55

CTC ACC GAC GAG ATT GTG AAG GAT GTG AAG CAG ACG TAC TTG GCA CGG      2584
Leu Thr Asp Glu Ile Val Lys Asp Val Lys Gln Thr Tyr Leu Ala Arg
        60                  65                  70

GTC TTC TCC TAC CCG GCA GGG AAT GTG GAG AGC ACC GGT TCT GCT GGG      2632
Val Phe Ser Tyr Pro Ala Gly Asn Val Glu Ser Thr Gly Ser Ala Gly
75                  80                  85                  90

GAG CCT CTG TAT GAG AAC TCC CCA GAG TTC ACA CCT TAC CTG GAG ACA      2680
Glu Pro Leu Tyr Glu Asn Ser Pro Glu Phe Thr Pro Tyr Leu Glu Thr
                95                 100                 105

AAC CTC GGA CAG CCA ACA ATT CAG AGT TTT GAA CAG GTG GGA ACA AAA      2728
Asn Leu Gly Gln Pro Thr Ile Gln Ser Phe Glu Gln Val Gly Thr Lys
            110                 115                 120

GTG AAT GTG ACC GTA GAA GAT GAA CGG ACT TTA GTC AGA AGG AAC AAC      2776
Val Asn Val Thr Val Glu Asp Glu Arg Thr Leu Val Arg Arg Asn Asn
            125                 130                 135

ACT TTC CTA AGC CTC CGG GAT GTT TTT GGC AAG GAC TTA ATT TAT ACA      2824
Thr Phe Leu Ser Leu Arg Asp Val Phe Gly Lys Asp Leu Ile Tyr Thr
        140                 145                 150

CTT TAT TAT TGG AAA TCT TCA AGT TCA GGA AAG AAA ACA GCC AAA ACA      2872
Leu Tyr Tyr Trp Lys Ser Ser Ser Ser Gly Lys Lys Thr Ala Lys Thr
155                 160                 165                 170

AAC ACT AAT GAG TTT TTG ATT GAT GTG GAT AAA GGA GAA AAC TAC TGT      2920
Asn Thr Asn Glu Phe Leu Ile Asp Val Asp Lys Gly Glu Asn Tyr Cys
            175                 180                 185

TTC AGT GTT CAA GCA GTG ATT CCC TCC CGA ACA GTT AAC CGG AAG AGT      2968
Phe Ser Val Gln Ala Val Ile Pro Ser Arg Thr Val Asn Arg Lys Ser
            190                 195                 200

ACA GAC AGC CCG GTA GAG TGT ATG GGC CAG GAG AAA GGG GAA TTC AGA      3016
Thr Asp Ser Pro Val Glu Cys Met Gly Gln Glu Lys Gly Glu Phe Arg
            205                 210                 215

GAA ATA TTC TAC ATC ATT GGA GCT GTG GTA TTT GTG GTC ATC ATC CTT      3064
Glu Ile Phe Tyr Ile Ile Gly Ala Val Val Phe Val Val Ile Ile Leu
        220                 225                 230

GTC ATC ATC CTG GCT ATA TCT CTA CAC AAG TGT AGA AAG GCA GGA GTG      3112
Val Ile Ile Leu Ala Ile Ser Leu His Lys Cys Arg Lys Ala Gly Val
235                 240                 245                 250

GGG CAG AGC TGG AAG GAG AAC TCC CCA CTG AAT GTT TCA TAAAGGAAGC       3161
Gly Gln Ser Trp Lys Glu Asn Ser Pro Leu Asn Val Ser
            255                 260

ACTGTTGGAG CTACTGCAAA TGCTATATTG CACTGTGACC GAGAACTTTT AAGAGGATAG   3221

AATACATGGA AACGCAAATG AGTATTTCGG AGCATGAAGA CCCTGGAGTT CAAAAAACTC   3281

TTGATATGAC CTGTTATTAC CATTAGCATT CTGGTTTTGA CATCAGCATT AGTCACTTTG   3341

AAATGTAACG AATGGTACTA CAACCAATTC CAAGTTTTAA TTTTTAACAC CATGGCACCT   3401

TTTGCACATA ACATGCTTTA GATTATATAT TCCGCACTTA AGGATTAACC AGGTCGTCCA   3461

AGCAAAAACA AATGGGAAAA TGTCTTAAAA AATCCTGGGT GGACTTTTGA AAAGCTCGAT   3521

CCGTCGAGGG ATCTTCCATA CCTACCAGTT CTGCGCCTGC AGGTCGCGGC CGCGACTCTA   3581

GAGGATCTTT GTGAAGGAAC CTTACTTCTG TGGTGTGACA TAATTGGACA AACTACCTAC   3641
```

-continued

```
AGAGATTTAA AGCTCTAAGG TAAATATAAA ATTTTTAAGT GTATAATGTG TTAAACTACT       3701

GATTCTAATT GTTGTGGTAT TTTAGATTCC AACCTATGGA ACTTATGAAT GGGAGCAGTG       3761

GTGGAATGCC TTTAATGAGG AAAACCTGTT TTGCTCAGAA GAAATGCCAT CTAGTGATGA       3821

TGAGGCTACT GCTGACTCTC AACATTCTAC TCCTCCAAAA AAGAAGAGAA AGGTAGAAGA       3881

CCCCAAGGAC TTTCCTTCAG AATTGGTAAG TTTTTTGAGT CATGCTGTGT TTAGTAATAG       3941

AACTCTTGCT TGCTTTGCTA TTTACACCAC AAAGGAAAAA GCTGCACTGC TATACAAGAA       4001

AATTATGGAA AAATATTCTG TAACCTTTAT AAGTAGGCAT AACAGTTATA ATCATAACAT       4061

ACTGTTTTTT CTTACTCCAC ACAGGCATAG AGTGTCTGCT ATTAATAACT ATGCTCAAAA       4121

ATTGTGTACC TTTAGCTTTT TAATTTGTAA AGGGGTTAAT AAGGAATATT TGATGTATAG       4181

TGCCTTGACT AGAGATCATA ATCAGCCATA CCACATTTGT AGAGGTTTTA CTTGCTTTAA       4241

AAAACCTCCC ACACCTCCCC CTGAACCTGA ACATAAAAT GAATGCAATT GTTGTTGTTA       4301

ACTTGTTTAT TGCAGCTTAT AATGGTTACA AATAAAGCAA TAGCATCACA AATTTCACAA       4361

ATAAAGCATT TTTATCACTG CATTCTAGTT GTGGTTTGTC CAAACTCATC AATGTATCTT       4421

ATCATGTCTG GATCCCGCCA TGGTATCAAC GCCATATTTC TATTTACAGT AGGGACCTCT       4481

TCGTTGTGTA GGTACCGCTG TATTCCTAGG GAAATAGTAG AGGCACCTTG AACTGTCTGC       4541

ATCAGCCATA TAGCCCCCGC TGTTCGACTT ACAAACACAG GCACAGTACT GACAAACCCA       4601

TACACCTCCT CTGAAATACC CATAGTTGCT AGGGCTGTCT CCGAACTCAT TACACCCTAC       4661

CAAGTGAGAG CTGTAATTTC GCGATCAAGG GCAGCGAGGG CTTCTCCAGA TAAAATAGCT       4721

TCTGCCGAGA GTCCCGTAAG GGTAGACACT TCAGCTAATC CCTCGATGAG GTCTACTAGA       4781

ATAGTCAGTG CGGCTCCCAT TTTGAAAATT CACTTACTTG ATCAGCTTCA GAAGATGGGC       4841

GAGGGCCTCC AACACAGTAA TTTTCCTCCC GACTCTTAAA ATAGAAAATG TCAAGTCAGT       4901

TAAGGAGGAA GTGGACTAAC TGACGGACCT GGCCGTGCGA CATCCTCTTT TAATTAGTTG       4961

CTAGGCAACG CCCTCCAGAG GGCGTGTGGT TTTGCAAGAG GAAGCAAAAG CCTCTCCACC       5021

CAGGCCTAGA ATGTTTCCAC CCAATCATTA CTATGACAAC AGCTGTTTTT TTAGTATTA       5081

AGCAGAGGCC GGGGACCCCT GGGCCCGCTT ACTCTGGAGA AAAAGAAGAG AGGCATTGTA       5141

GAGGCTTCCA GAGGCAACTT GTCAAAACAG GACTGCTTCT ATTTCTGTCA CACTGTCTGG       5201

CCCTGTCACA AGGTCCAGCA CCTCCATACC CCCTTTAATA AGCAGTTTGG GAACGGGTGC       5261

GGGTCTTACT CCGCCCATCC CGCCCCTAAC TCCGCCCAGT TCCGCCCATT CTCCGCCCCA       5321

TCGCTGACTA ATTTTTTTTA TTTATGCAGA GGCCGAGGCC GCCTCGGCCT CTGAGCTATT       5381

CCAGAAGTAG TGAGGAGGCT TTTTTGGAGG CCTAGGCTTT TGCAAAAAGC TAATTC         5437
```

(2) INFORMATION FOR SEQ ID NO:2:

(i) SEQUENCE CHARACTERISTICS:
        (A) LENGTH: 263 amino acids
        (B) TYPE: amino acid
        (D) TOPOLOGY: linear (ii) MOLECULE TYPE: protein (xi) SEQUENCE DESCRIPTION: SEQ ID NO:2:

```
Ser Gly Thr Thr Asn Thr Val Ala Ala Tyr Asn Leu Thr Trp Lys Ser
 1               5                  10                  15

Thr Asn Phe Lys Thr Ile Leu Glu Trp Glu Pro Lys Pro Val Asn Gln
            20                  25                  30

Val Tyr Thr Val Gln Ile Ser Thr Lys Ser Gly Asp Trp Lys Ser Lys
        35                  40                  45
```

```
Cys Phe Tyr Thr Thr Asp Thr Glu Cys Asp Leu Thr Asp Glu Ile Val
     50                  55                  60

Lys Asp Val Lys Gln Thr Tyr Leu Ala Arg Val Phe Ser Tyr Pro Ala
 65              70                  75                  80

Gly Asn Val Glu Ser Thr Gly Ser Ala Gly Glu Pro Leu Tyr Glu Asn
                 85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
            115                 120                 125

Asp Glu Arg Thr Leu Val Arg Arg Asn Asn Thr Phe Leu Ser Leu Arg
        130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
            195                 200                 205

Cys Met Gly Gln Glu Lys Gly Glu Phe Arg Glu Ile Phe Tyr Ile Ile
210                 215                 220

Gly Ala Val Val Phe Val Val Ile Ile Leu Val Ile Ile Leu Ala Ile
225                 230                 235                 240

Ser Leu His Lys Cys Arg Lys Ala Gly Val Gly Gln Ser Trp Lys Glu
                245                 250                 255

Asn Ser Pro Leu Asn Val Ser
            260

(2) INFORMATION FOR SEQ ID NO:3:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:3:

GGGGTATCTT TGGATAAAAG ATCAGGCACT ACAAATACTG TG                    42

(2) INFORMATION FOR SEQ ID NO:4:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:4:

GCAGCCAAGC TGGCCTCGAA GTTATCTGAA TTCCCCTTTC TCCTG                 45
```

(2) INFORMATION FOR SEQ ID NO:5:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:5:

```
CTAATTTCGC GACAATTT                                               18
```

(2) INFORMATION FOR SEQ ID NO:6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:6:

```
CTTGGAAAGC AGCTAATTTC GCGACAATTT                                  30
```

(2) INFORMATION FOR SEQ ID NO:7:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:7:

```
GTTCAAATAG CTGCTAAGGC AGGAGAT                                     27
```

(2) INFORMATION FOR SEQ ID NO:8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:8:

```
GAGATTGTGG CTGCAGTGGC GCAGACGTAC                                  30
```

(2) INFORMATION FOR SEQ ID NO:9:

-continued

```
    (i) SEQUENCE CHARACTERISTICS:
         (A) LENGTH: 5 amino acids
         (B) TYPE: amino acid
         (D) TOPOLOGY: linear (ii) MOLECULE TYPE: peptide (xi) SEQUENCE DESCRIPTION: SEQ ID NO:9:

Trp Ser Xaa Thr Ser
1               5
```